(12) United States Patent
Liang et al.

(10) Patent No.: US 7,629,339 B2
(45) Date of Patent: Dec. 8, 2009

(54) ALKOXY INDOLINONE BASED PROTEIN KINASE INHIBITORS

(75) Inventors: Congxin Liang, Jupiter, FL (US); Yangbo Feng, Palm Beach Gardens, FL (US)

(73) Assignee: The Scripps Research Institute, La Jolla, CA (US)

( * ) Notice: Subject to any disclaimer, the term of this patent is extended or adjusted under 35 U.S.C. 154(b) by 586 days.

(21) Appl. No.: 11/525,291

(22) Filed: Sep. 21, 2006

(65) Prior Publication Data

US 2007/0072934 A1  Mar. 29, 2007

Related U.S. Application Data

(60) Provisional application No. 60/719,474, filed on Sep. 22, 2005.

(51) Int. Cl.
*A61K 31/40* (2006.01)
*C07D 209/20* (2006.01)
*A61K 31/535* (2006.01)
*A61K 31/445* (2006.01)
*C07D 401/14* (2006.01)
*C07D 413/14* (2006.01)

(52) U.S. Cl. ............ 514/235.2; 548/468; 514/414; 514/323; 544/144; 546/187

(58) Field of Classification Search ............ 514/414, 514/235.2, 323; 548/468; 546/187; 544/144
See application file for complete search history.

(56) References Cited

U.S. PATENT DOCUMENTS 6,653,308 B2  11/2003  Guan et al.

OTHER PUBLICATIONS

McMahon, et al., "Protein Kinase Inhibitors: Structural Determinants for Target Specificity" *Curr. Opin. Drug Disc. Dev. 1*: 131-146 (1998).
Sun, et al., "Synthesis and Biological Evaluations of 3-Substituted Indolin-2-ones: A Novel Class of Tyrosine Kinase Inhibitors That Exhibit Selectivity toward Particular Receptor Tyrosine Kinases", *J. Med. Chem. 41*: 2588-2603 (1998).
Sun, et al., "Design, Synthesis, and Evaluations of Substituted 3-[(3- or 4-Carboxyethylpyrrol-2-yl)methylidenyl]indolin-2-ones as Inhibitors of VEGF, FGF, and PDGF Receptor Tyrosine Kinases", *J. Med. Chem. 42*: 5120-5130 (1999).
Laird, et al., "SU6668 Is a Potent Antiangiogenic and Antitumor Agent That Induces Regression of Established Tumors", *Cancer Res. 60*: 4152-4160 (2000).
Smolich, et al., "The antiangiogenic protein kinase inhibitors SU5416 and SU6668 inhibit the SCF receptor (c-kit) in a human myeloid leukemia cell line and in acute myeloid leukemia blasts", *Blood 97*: 1413-1421 (2001).
Laird, et al., "SU6668 inhibits Flk-1/KDR and PDGFRβ in vivo, resulting in rapid apoptosis of tumor vasculature and tumor regression in mice", *FASEB J. 16*: 681-690 (2002).
Mendel, et al., "In Vivo Antitumor Activity of SU11248, a Novel Tyrosine Kinase Inhibitor Targeting Vascular Endothelial Growth Factor and Platelet-derived Growth Factor Receptors: Determination of a Pharmacokinetic/Pharmacodynamic Relationship", *Clin. Cancer Res. 9*: 327-337 (2003).
Sun, et al., "Discovery of 5-[5-Fluoro-2-oxo-1,2-dihydroindol-(3Z)-ylidenemethyl]-2,4-dimethyl-1*H*-pyrrole-3-carboxylic Acid (2-Diethylaminoethyl)amide, a Novel Tyrosine Kinase Inhibitor Targeting Vascular Endothelial and Platelet-Derived Growth Factor Receptor Tyrosine Kinase", *J. Med. Chem. 46*: 1116-1119 (2003).

*Primary Examiner*—Rebecca L Anderson
(74) *Attorney, Agent, or Firm*—Schwegman, Lundberg & Woessner, P.A.

(57) ABSTRACT

Alkoxy indolinone based acid and amide derivatives have enhanced and unexpected drug properties as inhibitors of protein kinases and are useful in treating disorders related to abnormal protein kinase activities such as cancer.

31 Claims, 3 Drawing Sheets

ALKOXY INDOLINONE BASED PROTEIN KINASE INHIBITORS

FIELD OF INVENTION

The invention relates to protein kinase inhibitors and to their use in treating disorders related to abnormal protein kinase activities such as cancer and inflammation. More particularly, the invention relates to alkoxy indolinone based derivatives and their pharmaceutically acceptable salts employable as protein kinase inhibitors.

BACKGROUND

Protein kinases are enzymes that catalyze the phosphorylation of hydroxyl groups of tyrosine, serine, and threonine residues of proteins. Many aspects of cell life (for example, cell growth, differentiation, proliferation, cell cycle and survival) depend on protein kinase activities. Furthermore, abnormal protein kinase activity has been related to a host of disorders such as cancer and inflammation. Therefore, considerable effort has been directed to identifying ways to modulate protein kinase activities. In particular, many attempts have been made to identify small molecules that act as protein kinase inhibitors.

Several pyrrolyl-indolinone derivatives have demonstrated excellent activity as inhibitors of protein kinases (Larid et al. FASEB J. 16, 681, 2002; Smolich et al. Blood, 97, 1413, 2001; Mendel et al. Clinical Cancer Res. 9, 327, 2003; Sun et al. J. Med. Chem. 46, 1116, 2003). The clinical utility of these compounds has been promising, but has been partially compromised due to the relatively poor aqueous solubility and/or other drug properties. What is needed is a class of modified pyrrolyl-indolinone derivatives having both inhibitory activity and enhanced drug properties.

SUMMARY

The invention is directed to alkoxy indolinone based derivatives and to their use as inhibitors of protein kinases. It is disclosed herein that alkoxy indolinone based derivatives have enhanced and unexpected drug properties that advantageously distinguish this class of compounds over known pyrrolyl-indolinone derivatives having protein kinase inhibition activity. It is also disclosed herein that alkoxy indolinone based derivatives are useful in treating disorders related to abnormal protein kinase activities such as cancer.

One aspect of the invention is directed to a compound represented by Formula (I):

Formula I

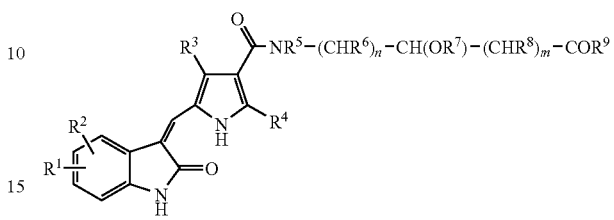

In Formula (I), $R^1$ is selected from the group consisting of hydrogen, halo, (C1-C6) alkyl, (C3-C8) cycloalkyl, (C1-C6) haloalkyl, hydroxy, (C1-C6) alkoxy, amino, (C1-C6) alkylamino, amide, sulfonamide, cyano, substituted or unsubstituted (C6-C10) aryl; $R^2$ is selected from the group consisting of hydrogen, halo, (C1-C6) alkyl, (C3-C8) cycloalkyl, (C1-C6) haloalkyl, hydroxy, (C1-C6) alkoxy, (C2-C8) alkoxyalkyl, amino, (C1-C6) alkylamino, (C6-C10) arylamino; $R^3$ is selected from the group consisting of hydrogen, (C1-C6) alkyl, (C6-C10) aryl, (C5-C10) heteroaryl, and amide; $R^4$, $R^5$, $R^6$ and $R^8$ are independently selected from the group consisting of hydrogen and (C1-C6) alkyl; $R^7$ is (C1-C6) alkyl; $R^9$ is selected from the group consisting of hydroxy, (C1-C6) O-alkyl, (C3-C8) O-cycloalkyl, and $NR^{10}R^{11}$; where $R^{10}$ and $R^{11}$ are independently selected from the group consisting of hydrogen, (C1-C6) alkyl, (C1-C6) hydroxyalkyl, (C2-C6) dihydroxyalkyl, (C1-C6) alkoxy, (C1-C6) alkyl carboxylic acid, (C1-C6) alkyl phosphonic acid, (C1-C6) alkyl sulfonic acid, (C1-C6) hydroxyalkyl carboxylic acid, (C1-C6) alkyl amide, (C3-C8) cycloalkyl, (C5-C8) heterocycloalkyl, (C6-C8) aryl, (C5-C8) heteroaryl, (C3-C8) cycloalkyl carboxylic acid, or $R^{10}$ and $R^{11}$ together with N forms a (C5-C8) heterocyclic ring either unsubstituted or substituted with one or more hydroxyls, ketones, ethers, and carboxylic acids; n is 1, 2, or 3; and m is 0, 1, or 2. Alternatively, this aspect of the invention also is directed to a pharmaceutically acceptable salt, its tautomer, a pharmaceutically acceptable salt of its tautomer, or a prodrug of Formula (I).

A first preferred subgenus of this first aspect of the invention is directed to the compound, salt, tautomer, or prodrug represented by Formula (II):

Formula II

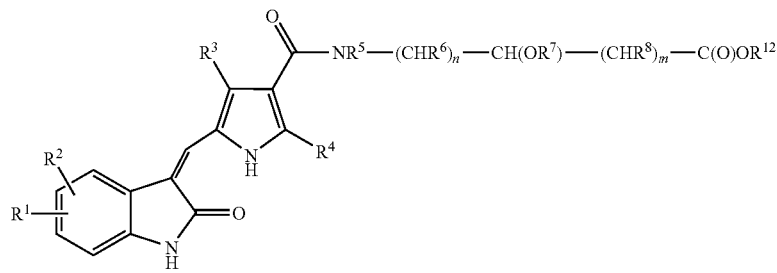

In Formula (II), $R^{12}$ is selected from the group consisting of hydrogen, (C1-C6) alkyl, and (C3-C8) cycloalkyl. Other groups are as defined in Formula (I). In preferred embodiments, $R^1$ and $R^2$ are independently selected from the group consisting of hydrogen and fluoro; $R^3$ and $R^4$ are methyl; $R^5$, $R^6$, $R^8$, and $R^{12}$ are hydrogen; $R^7$ is (C1-C6) alkyl; n is 1 or 2; and m is 0 or 1. Preferred species include the following compounds:

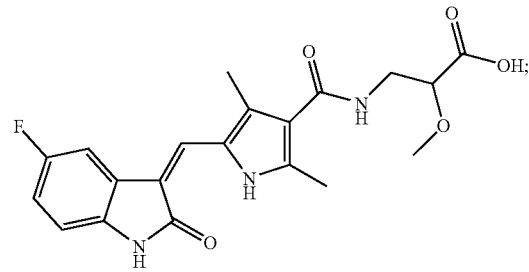

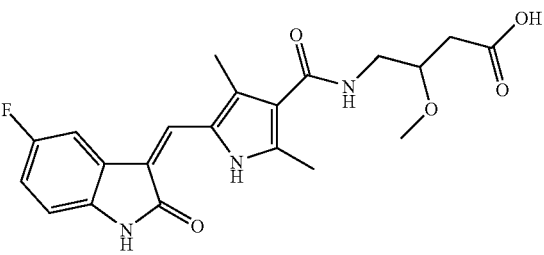

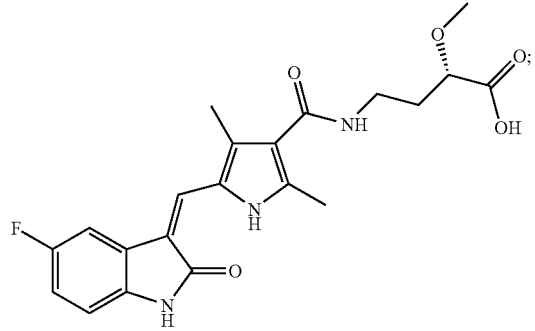

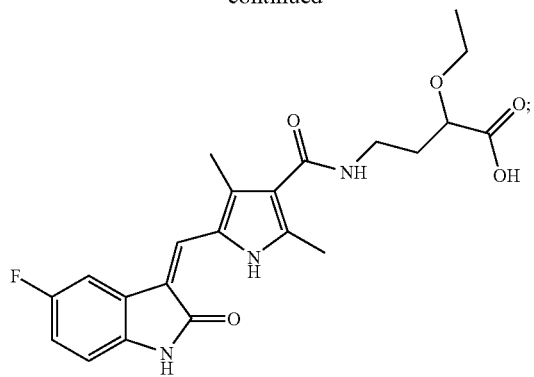

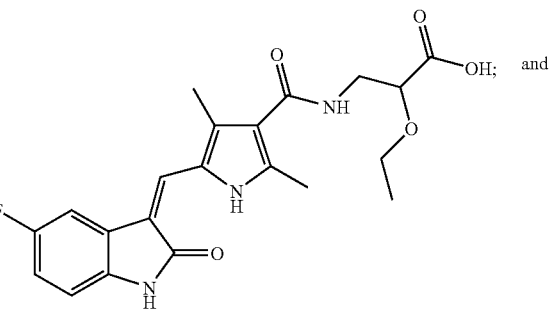

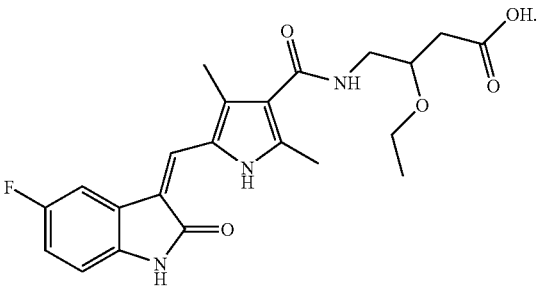

A second preferred subgenus of this first aspect of the invention is directed to a compound, salt, tautomer, or prodrug represented by Formula (III):

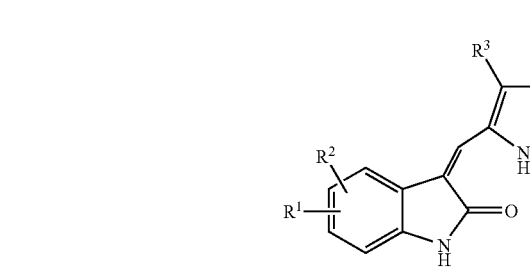

Formula III

In Formula (III), the various R groups are the same as Formula (I). In preferred embodiments, $R^1$ and $R^2$ are independently selected from the group consisting of hydrogen, halo, cyano; $R^3$ is selected from the group consisting of hydrogen, (C1-C6) alkyl, (C6-C10) aryl, (C5-C10) heteroaryl, and amide; $R^4$, $R^5$, $R^6$ and $R^8$ are independently selected from the group consisting of hydrogen and (C1-C6) )alkyl; $R^7$ is (C1-C6) alkyl; n is 1 or 2; m is 0 or 1; and $R^{10}$ and $R^{11}$ are selected from the group consisting of hydrogen, (C1-C6) alkyl, (C1-C6) hydroxyalkyl, (C2-C6) dihydroxyalkyl, (C1-C6) alkoxy, (C2-C6) alkyl carboxylic acid, (C1-C6) alkyl phosphonic acid, (C1-C6) alkyl sulfonic acid, (C2-C6) hydroxyalkyl carboxylic acid, (C1-C6) alkyl amide, (C3-C8) cycloalkyl, (C5-C8) heterocycloalkyl, (C6-C8) aryl, (C5-C8) heteroaryl, (C4-C8) cycloalkyl carboxylic acid, or $R^{10}$ and $R^{11}$ together with N forms a (C5-C8) heterocyclic ring either unsubstituted or substituted with one or more hydroxyls, ketones, ethers, and carboxylic acids.

In a first subgroup of this second subgenus, m is 0. Preferred species of this first subgroup are represented by the following structures:

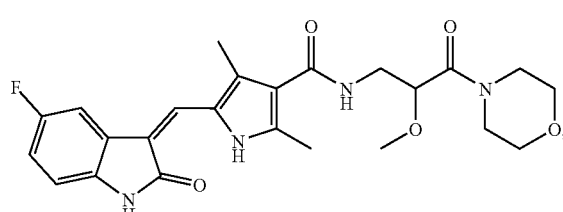

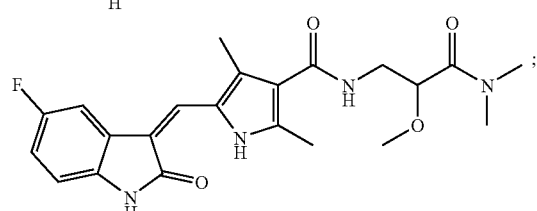

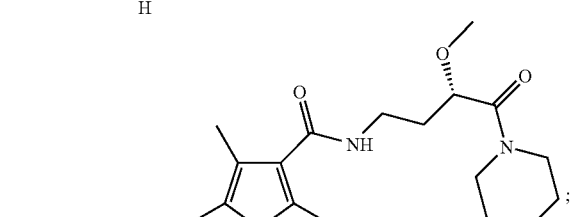

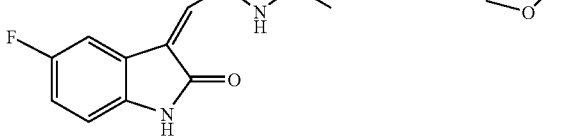

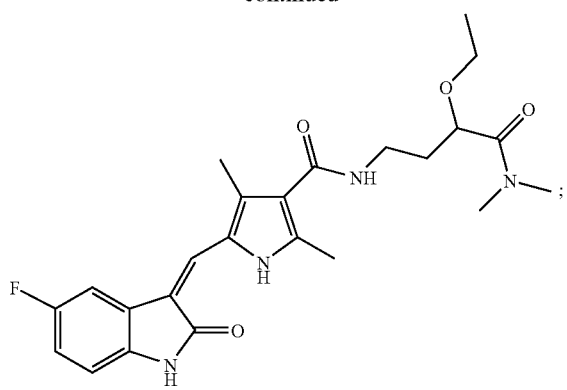

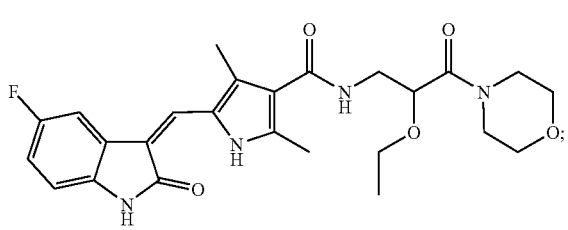

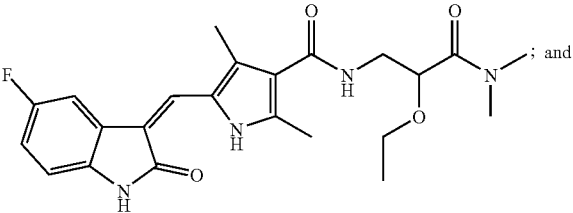

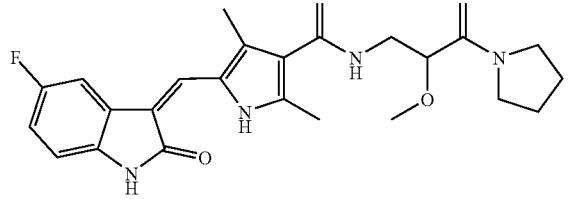

In a second subgroup of this second subgenus, m is 1. Preferred species of this second subgroup are represented by the following structures:

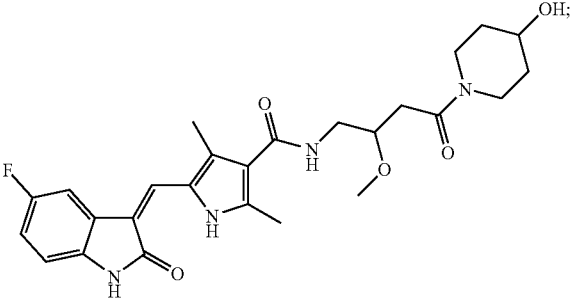

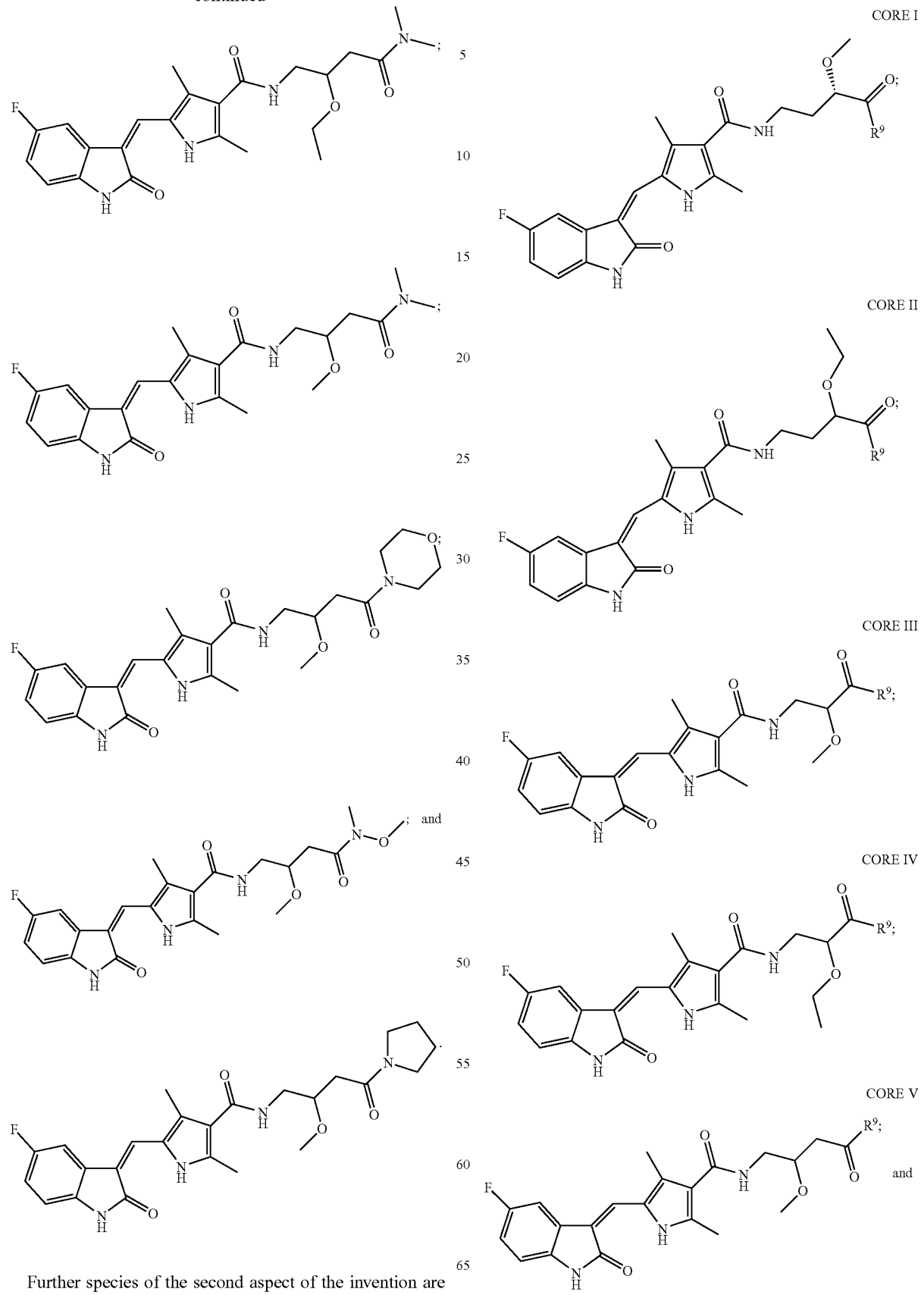
Further species of the second aspect of the invention are represented by the following structures:

CORE VI

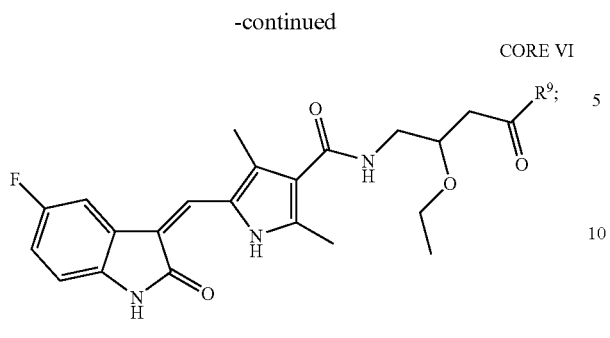

wherein: $R^9$ is selected from the group consisting of radicals represented by the following structures:

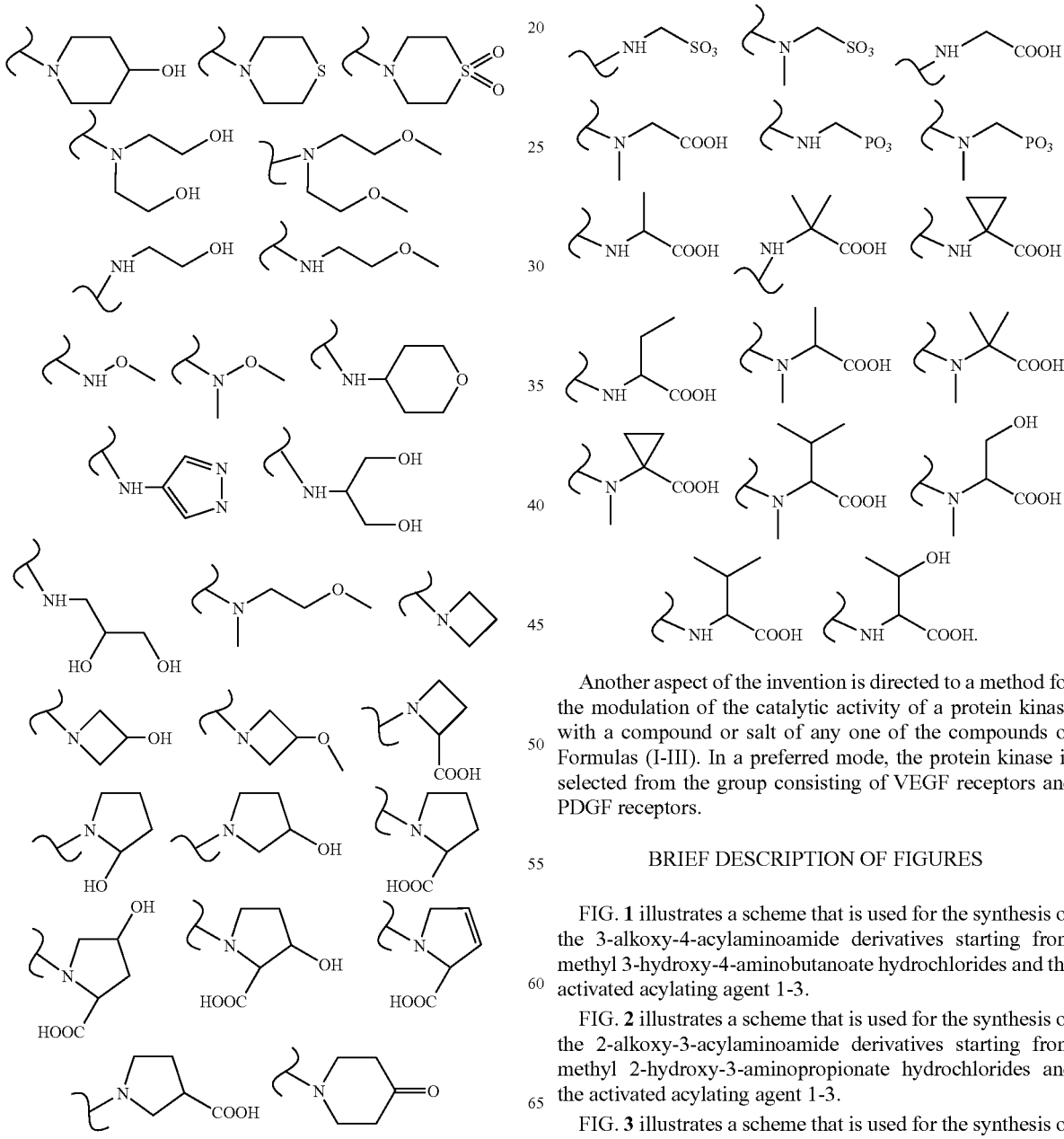
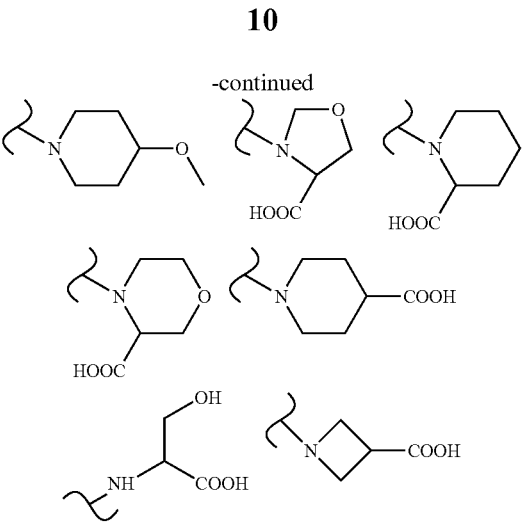

Another aspect of the invention is directed to a method for the modulation of the catalytic activity of a protein kinase with a compound or salt of any one of the compounds of Formulas (I-III). In a preferred mode, the protein kinase is selected from the group consisting of VEGF receptors and PDGF receptors.

DETAILED DESCRIPTION

Examples 1-8

Figure 1:
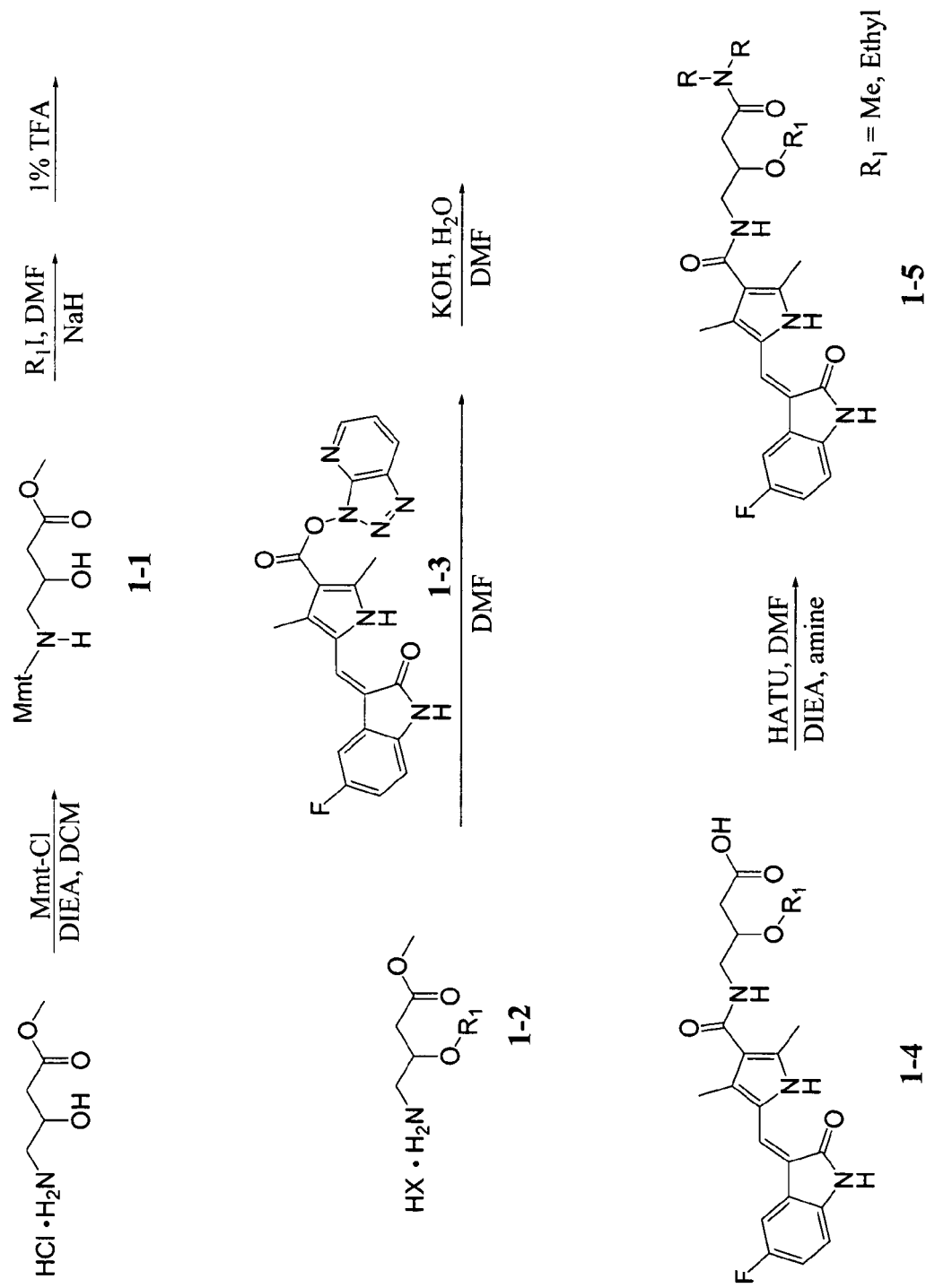
FIG. 1 illustrates a scheme that is used for the synthesis of the 3-alkoxy-4-acylaminoamide derivatives starting from methyl 3-hydroxy-4-aminobutanoate hydrochlorides and the activated acylating agent 1-3.

The synthesis of acids (1-4) and amides (1-5) is shown in FIG. 1. Variations from this general synthetic procedure can be understood and carried out by those skilled in the art. Thus, the compounds of the present invention can be synthesized by those skilled in the art.

Example 1

4-({5-[5-Fluoro-2-oxo-1,2-dihydro-indol-(3Z)-ylidenemethyl]-2,4-dimethyl-1H-pyrrole-3-carbonyl}-amino)-3-methoxy-butyric acid

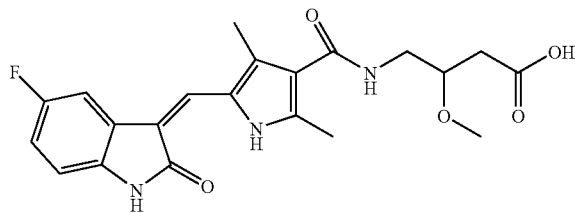

To a suspension of methyl 4-amino-3-hydroxybutyrate (1.0 equiv, which was prepared by refluxing the free amino acid in dry methanol with 1.2 equiv HCl) and DIEA (5 equiv) in DCM, Mmt-Cl (1.1 equiv) was added portion-wise at 25° C. After stirring overnight, the DCM was removed under reduced pressure. The residue was suspended in ethyl acetate, washed with brine (3×), dried over anhydrous $Na_2SO_4$. The ethyl acetate was then removed, and the residue was dried overnight under high vacuum, and subjected to flash chromatography to give compound 1-1. To a solution of compound 1-1 in dry DMF, NaH (1.5 equiv) was added under argon. After stirring at 25° C. for 1 h, MeI (5 equiv) was added to the solution, and the resulting suspension was gently shaken at 25° C. overnight. The DMF was removed under vacuum; the residue was suspended in ethyl acetate, washed with brine (3×), and dried over anhydrous $Na_2SO_4$. After the ethyl acetate was removed via evaporation the resulting residue was treated with 1% TFA in DCE/DCM for 30 min. The organic solvents were then removed under reduced pressure, and the resulting residue was triturated with hexane (3×) to obtain the free amino acid 1-2. This amino acid was used directly in the next step without any purification and characterization. Thus, to a solution of 1-2 (2 equiv) and DIEA (5 equiv) in DMF, compound 1-3 (1 equiv) was added at 25° C. After stirring for 30 min (LC-MS show the complete consumption of 1-3), KOH (5 equiv) in water was added, and the solution was stirred for another 2 h (LC-MS demonstrated a complete hydrolysis). The solvents were removed under reduced pressure, and HCl (1N, excess) was added to give a precipitate. This precipitate was collected and washed (by water) by filtration, dried under high vacuum to give the title compound (95% based on compound 1-3). LC-MS: single peak at 254 nm, MH$^+$ calcd. for $C_{21}H_{22}FN_3O_5$: 416, obtained: 416. $^1$H-NMR (DMSO-d$_6$, 400 MHz), δ 13.67 (s, 1H), 12.18 (b, 1H), 10.90 (s, 1H), 7.75 (dd, J=2.4 Hz, J=9.6 Hz, 1H), 7.71 (s, 1H), 7.64 (t, J=6.0 Hz, 1H), 6.92 (m, 1H) 6.83 (dd, J=4.8 Hz, J=8.4 Hz, 1H), 3.73 (m, 1H), 3.43-3.31 (m, 2H), 3.22 (s, 3H), 2.52-2.35 (m, 2H), 2.43 (s, 3H), 2.41 (s, 3H).

Example 2

3-Ethoxy-4-({5-[5-fluoro-2-oxo-1,2-dihydro-indol-(3Z)-ylidenemethyl]-2,4-dimethyl-1H-pyrrole-3-carbonyl}-amino)-butyric acid

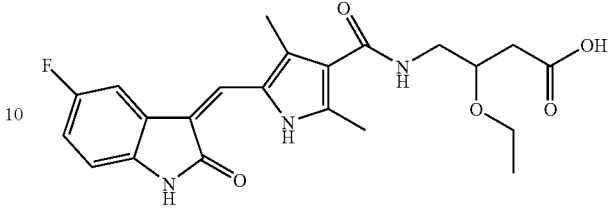

A similar route as that for the synthesis of Example 1 was used to prepare the title compound. Iodoethane was used instead of iodomethane to obtain the 3-ethoxy compound (9.7% based on compound 1-3). LC-MS: single peak at 254 nm, MH$^+$ calcd. for $C_{22}H_{24}FN_3O_5$: 430, obtained: 430.

Examples 3-8

The general procedure for the synthesis of amides (1-5): An amine (2 equiv) was added to a solution of the acid (1-4), HATU (1.05 mmol), and DIEA (5 equiv) in DMF (5 mL). After the solution was stirred at 25° C. for 2 h, aqueous HCl (2 mL, 1N) was added. This solution was subjected to preparative HPLC to obtain the pure amide product, which was subsequently characterized by LC-MS and NMR spectroscopy.

Example 3

5-[5-Fluoro-2-oxo-1,2-dihydro-indol-(3Z)-ylidenemethyl]-2,4-dimethyl-1H-pyrrole-3-carboxylic acid (3-dimethylcarbamoyl-2-ethoxy-propyl)-amide

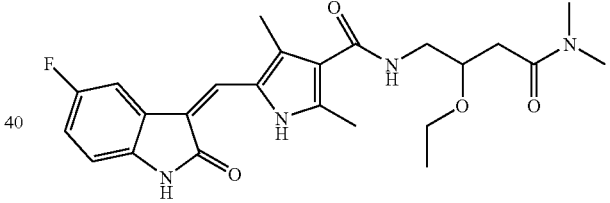

Preparative HPLC gave 13 mg of the title compound (41%) from 30 mg starting material (acid). LC-MS: single peak at 254 nm, MH$^+$ calcd. for $C_{24}H_{29}FN_4O_4$: 457, obtained: 457. $^1$H-NMR (DMSO-d$_6$, 400 MHz), δ 13.68 (s, 1H), 10.89 (s, 1H), 7.76 (dd, J=2.4 Hz, 9.2 Hz, 1H), 7.72 (s, 1H), 7.60 (t, J=6.0 Hz, 1H), 6.92 (m, 1H) 6.83 (dd, J=4.8 Hz, 8.4 Hz, 1H), 3.89 (m, 1H), 3.58-3.45 (m, 2H), 3.40-3.27 (m, 2H, buried in water signals), 2.97 (s, 3H), 2.82 (s, 3H), 2.43 (s, 3H), 2.41 (s, 3H), 1.07 (t, J=7.2 Hz, 3H).

Example 4

5-[5-Fluoro-2-oxo-1,2-dihydro-indol-(3Z)-ylidenemethyl]-2,4-dimethyl-1H-pyrrole-3-carboxylic acid (3-dimethylcarbamoyl-2-methoxy-propyl)-amide

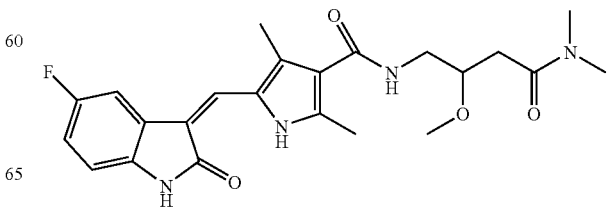

Preparative HPLC gave 46 mg of the title compound (36%) from 120 mg starting material (acid). LC-MS: single peak at 254 nm, MH+ calcd. for $C_{23}H_{27}FN_4O_4$: 443, obtained: 443. $^1$H-NMR (DMSO-d$_6$, 400 MHz), δ 13.68 (s, 1H), 10.89 (s, 1H), 7.76 (dd, J=2.4 Hz, 9.2 Hz, 1H), 7.71 (s, 1H), 7.63 (t, J=5.6 Hz, 1H), 6.92 (m, 1H), 6.83 (dd, J=4.8 Hz, 8.8 Hz, 1H), 3.78 (m, 1H), 3.42-3.31 (m, 2H), 3.30 (s, 3H), 2.97 (s, 3H), 2.82 (s, 3H), 2.43 (s, 3H), 2.41 (s, 3H), 2.63-2.43 (m, 2H).

Example 5

5-[5-Fluoro-2-oxo-1,2-dihydro-indol-(3Z)-ylidenemethyl]-2,4-dimethyl-1H-pyrrole-3-carboxylic acid (2-methoxy-4-morpholin-4-yl-4-oxo-butyl)-amide

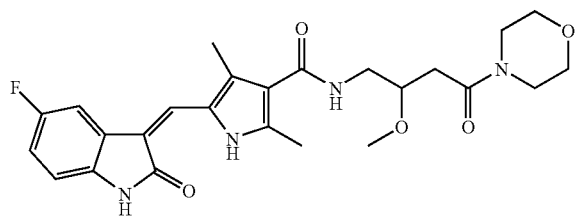

Preparative HPLC gave 48 mg of the title compound (37%) from 110 mg starting material (acid). LC-MS: single peak at 254 nm, MH+ calcd. for $C_{25}H_{29}FN_4O_6$: 485, obtained: 485. $^1$H-NMR (DMSO-d$_6$, 400 MHz), δ 13.68 (s, 1H), 10.89 (s, 1H), 7.76 (dd, J=2.4 Hz, 9.2 Hz, 1H), 7.71 (s, 1H), 7.63 (t, J=5.6 Hz, 1H), 6.92 (m, 1H), 6.83 (dd, J=4.8 Hz, 8.4 Hz, 1H), 3.80 (m, 1H), 3.55 (m, 4H), 3.47 (m, 4H), 3.38 (m, 2H), 3.31 (s, 3H), 2.60 (m, 1H), 2.45 (m, 1H), 2.43 (s, 3H), 2.41 (s, 3H).

Example 6

5-[5-Fluoro-2-oxo-1,2-dihydro-indol-(3Z)-ylidenemethyl]-2,4-dimethyl-1H-pyrrole-3-carboxylic acid [4-(4-hydroxy-piperidin-1-yl)-2-methoxy-4-oxo-butyl]-amide

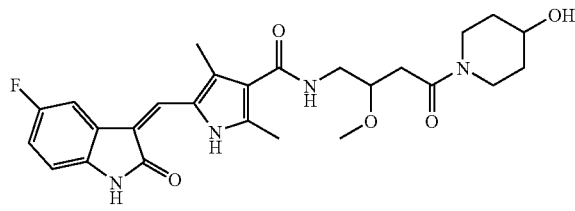

Preparative HPLC gave 20 mg of the title compound (33%) from 50 mg starting material (acid). LC-MS: single peak at 254 nm, MH+ calcd. for $C_{26}H_{31}FN_4O_5$: 499, obtained: 499. $^1$H-NMR (DMSO-d$_6$, 400 MHz), δ 13.68 (s, 1H), 10.89 (s, 1H), 7.76 (dd, J=2.4 Hz, 9.6 Hz, 1H), 7.72 (s, 1H), 7.63 (t, J=5.6 Hz, 1H), 6.93 (m, 1H), 6.83 (dd, J=4.4 Hz, 8.4 Hz, 1H), 3.92 (m, 1H), 3.78 (m, 1H), 3.68 (b, 1H), 3.30 (s, 3H), 3.15 (m, 1H), 3.01 (m, 1H), 2.60 (m, 1H), 2.55 (m, 2H), 2.50 (m, 1H), 2.45 (m, 2H), 2.43 (s, 3H), 2.41 (s, 3H), 1.70 (m, 2H), 1.30 (m, 2H).

Example 7

5-[5-Fluoro-2-oxo-1,2-dihydro-indol-(3Z)-ylidenemethyl]-2,4-dimethyl-1H-pyrrole-3-carboxylic acid (2-methoxy-4-oxo-4-pyrrolidin-1-yl-butyl)-amide

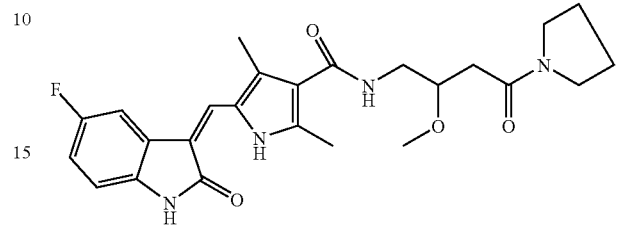

Preparative HPLC gave 40 mg of the title compound (32%) from 110 mg starting material (acid). LC-MS: single peak at 254 nm, MH+ calcd. for $C_{25}H_{29}FN_4O_4$: 469, obtained: 469. $^1$H-NMR (DMSO-d$_6$, 400 MHz), δ 13.68 (s, 1H), 10.89 (s, 1H), 7.76 (dd, J=2.4 Hz, 9.6 Hz, 1H), 7.71 (s, 1H), 7.63 (t, J=5.6 Hz, 1H), 6.93 (m, 1H), 6.83 (dd, J=4.8 Hz, 8.8 Hz, 1H), 3.82 (m, 1H), 3.50-3.25 (m, 6H), 3.30 (s, 3H), 2.55-2.45 (m, 2H), 2.43 (s, 3H), 2.41 (s, 3H), 1.86 (m, 2H), 1.76 (m, 2H).

Example 8

5-[5-Fluoro-2-oxo-1,2-dihydro-indol-(3Z)-ylidenemethyl]-2,4-dimethyl-1H-pyrrole-3-carboxylic acid[2-methoxy-3-(methoxy-methyl-carbamoyl)-propyl]-amide

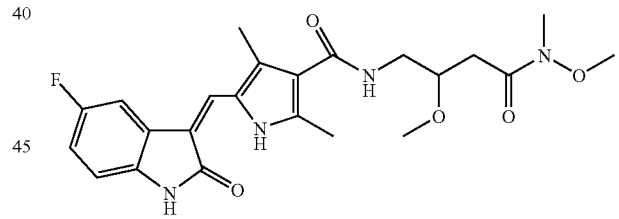

Preparative HPLC gave 15 mg of the title compound (15%) from 80 mg starting material (acid). LC-MS: single peak at 254 nm, MH+ calcd. for $C_{23}H_{27}FN_4O_5$: 459, obtained: 459. $^1$H-NMR (DMSO-d$_6$, 400 MHz), δ 13.68 (s, 1H), 10.90 (s, 1H), 7.76 (dd, J=2.4 Hz, 9.2 Hz, 1H), 7.72 (s, 1H), 7.68 (t, J=6.0 Hz, 1H), 6.93 (m, 1H), 6.84 (dd, J=4.4 Hz, 8.4 Hz, 1H), 3.79 (m, 1H), 3.66 (s, 3H), 3.50-3.35 (m, 2H), 3.31 (s, 3H), 3.13 (s, 3H), 2.55-2.45 (m, 2H), 2.43 (s, 3H), 2.41 (s, 3H).

Examples 9-15

Figure 2:
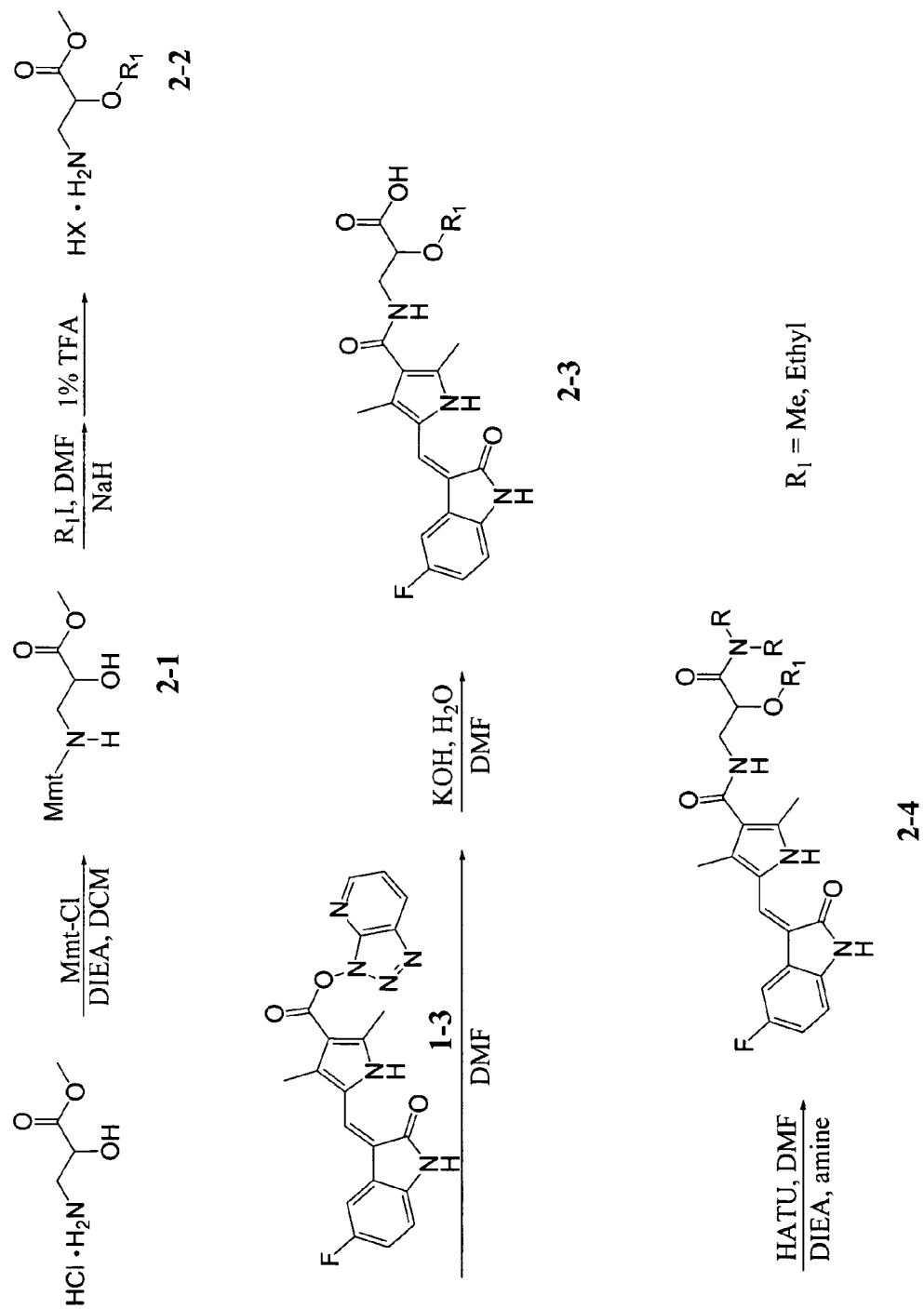
FIG. 2 illustrates a scheme that is used for the synthesis of the 2-alkoxy-3-acylaminoamide derivatives starting from methyl 2-hydroxy-3-aminopropionate hydrochlorides and the activated acylating agent 1-3.

The synthesis of acids (2-3) and amides (2-4) is shown in FIG. 2. Variations from this general synthetic procedure can be understood and carried out by those skilled in the art. Thus, the compounds of the present invention can be synthesized by those skilled in the art.

Example 9

3-({5-[5-Fluoro-2-oxo-1,2-dihydro-indol-(3Z)-ylidenemethyl]-2,4-dimethyl-1H-pyrrole-3-carbonyl}-amino)-2-methoxy-propionic acid

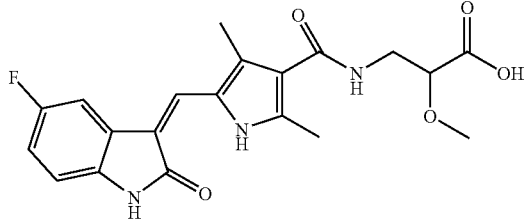

To a suspension of methyl 3-amino-2-hydroxypropionate (1.0 equiv, which was prepared by refluxing the free amino acid isoserine in dry methanol with 1.2 equiv HCl) and DIEA (5 equiv) in DCM, Mmt-Cl (1.1 equiv) was added portionwise at 25° C. After stirring overnight, the DCM was removed under reduced pressure. The residue was suspended in ethyl acetate, washed with brine (3×), dried over anhydrous $Na_2SO_4$. The ethyl acetate was then removed, and the residue was dried overnight under high vacuum, and subjected to flash chromatography to give compound 2-1. To a solution of compound 2-1 in dry DMF, NaH (1.5 equiv) was added under argon. After stirring at 25° C. for 1 h, MeI (5 equiv) was added to the solution, and the resulting suspension was gently stirred at 25° C. overnight. The DMF was removed under vacuum; the residue was suspended in ethyl acetate, washed with brine (3×), and dried over anhydrous $Na_2SO_4$. After the ethyl acetate was removed via evaporation the resulting residue was treated with 1% TFA in DCE/DCM for 30 min. The organic solvents were then removed under reduced pressure, and the resulting residue was triturated with hexane (3×) to obtain the free amino acid 2-2. This amino acid was used directly in the next step without any purification and characterizations. Thus, to a solution of 2-2 (2 equiv) and DIEA (5 equiv) in DMF, compound 1-3 (1 equiv) was added at 25° C. After stirring for 30 min (LC-MS show the complete consumption of 1-3), KOH (5 equiv) in water was added, and the solution was stirred for another 2 h (LC-MS demonstrated a complete hydrolysis). The solvents were removed under reduced pressure, and HCl (1N, excess) was added to give a precipitate. This precipitate was collected by filtration, washed with water and dried under high vacuum to give the title compound (99% based on compound 1-3). LC-MS: single peak at 254 nm, MH+ calcd. for $C_{20}H_{20}FN_3O_5$: 402, obtained: 402. $^1$H-NMR (DMSO-$d_6$, 400 MHz), δ 13.67 (s, 1H), 12.83 (b, 1H), 10.90 (s, 1H), 7.76 (dd, J=2.4 Hz, J=9.6 Hz, 1H), 7.71 (s, 1H), 7.69 (t, J=6.0 Hz, 1H), 6.92 (m, 1H), 6.82 (dd, J=4.8 Hz, J=8.4 Hz, 1H), 3.90 (m, 1H), 3.55 (m, 1H), 3.41 (m, 1H), 3.32 (s, 3H), 2.42 (s, 3H), 2.40 (s, 3H).

Example 10

2-Ethoxy-3-({5-[5-fluoro-2-oxo-1,2-dihydro-indol-(3Z)-ylidenemethyl]-2,4-dimethyl-1H-pyrrole-3-carbonyl}-amino)-propionic acid

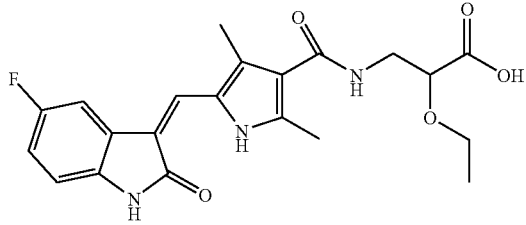

A similar route as that for the synthesis of Example 9 was used to prepare the title compound. Iodoethane was used instead of iodomethane to obtain the 2-ethoxy compound (38% based on compound 1-3). LC-MS: single peak at 254 nm, MH+ calcd. for $C_{21}H_{22}FN_4O_5$: 416, obtained: 416. $^1$H-NMR (DMSO-$d_6$, 400 MHz), δ 13.67 (s, 1H), 12.80 (b, 1H), 10.89 (s, 1H), 7.76 (dd, J=2.4 Hz, J=9.2 Hz, 1H), 7.71 (s, 1H), 7.68 (t, J=6.0 Hz, 1H), 6.92 (m, 1H), 6.83 (dd, J=4.8 Hz, J=8.4 Hz, 1H), 4.00 (dd, J=5.2 Hz, J=7.6 Hz, 1H), 3.58 (m, 2H), 3.41 (m, 2H), 2.43 (s, 3H), 2.41 (s, 3H), 1.14 (t, J=6.8 Hz, 3H).

Examples 11-15

The general procedure for the synthesis of amides (compounds 2-4): A corresponding amine (2 equiv) was added to a solution of the acid (compound 2-3), HATU (1.05 mmol), and DIEA (5 equiv) in DMF (5 mL). After the solution was stirred at 25° C. for 2 h, aqueous HCl (2 mL, 1N) was added. This solution was subjected to preparative HPLC to obtain the pure amide product, which was subsequently characterized by LC-MS and NMR spectroscopy.

Example 11

5-[5-Fluoro-2-oxo-1,2-dihydro-indol-(3Z)-ylidenemethyl]-2,4-dimethyl-1H-pyrrole-3-carboxylic acid (2-dimethylcarbamoyl-2-ethoxy-ethyl)-amide

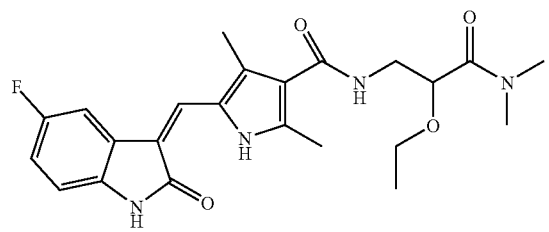

Preparative HPLC gave 46 mg of the title compound (62%) from 70 mg starting material (acid). LC-MS: single peak at 254 nm, MH+ calcd. for $C_{23}H_{27}FN_4O_4$: 443, obtained: 443.

Example 12

5-[5-Fluoro-2-oxo-1,2-dihydro-indol-(3Z)-ylidenemethyl]-2,4-dimethyl-1H-pyrrole-3-carboxylic acid (2-ethoxy-3-morpholin-4-yl-3-oxo-propyl)-amide

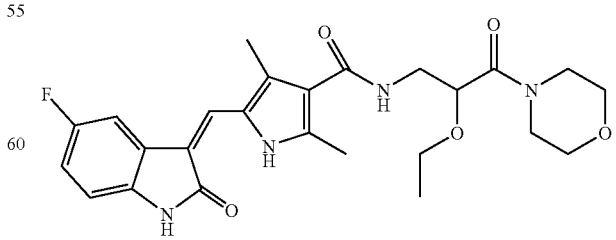

Preparative HPLC gave 40 mg of the title compound (49%) from 70 mg starting material (acid). LC-MS: single peak at 254 nm, MH+ calcd. for $C_{25}H_{29}FN_4O_5$: 485, obtained: 485. $^1$H-NMR (DMSO-d$_6$, 400 MHz), δ 13.67 (s, 1H), 10.89 (s, 1H), 7.76 (dd, J=2.4 Hz, J=9.6 Hz, 1H), 7.71 (s, 1H), 7.70 (m, 1H), 6.93 (m, 1H), 6.83 (dd, J=4.8 Hz, J=8.4 Hz, 1H), 4.40 (m, 1H), 3.73-3.35 (m, 12H), 2.43 (s, 3H) 2.41 (s, 3H), 1.12 (t, J=7.2 Hz, 3H).

Example 13

5-[5-Fluoro-2-oxo-1,2-dihydro-indol-(3Z)-ylidenemethyl]-2,4-dimethyl-1H-pyrrole-3-carboxylic acid (2-dimethylcarbamoyl-2-methoxy-ethyl)-amide

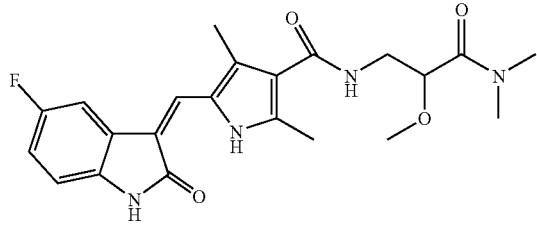

Preparative HPLC gave 93 mg of the title compound (76%) from 115 mg starting material (acid). LC-MS: single peak at 254 nm, MH+ calcd. for $C_{22}H_{25}FN_4O_4$: 429, obtained: 429. $^1$H-NMR (DMSO-d$_6$, 400 MHz), δ 13.68 (s, 1H), 10.90 (s, 1H), 7.75 (dd, J=2.4 Hz, J=9.6 Hz, 1H), 7.72 (m, 1H), 7.71 (s, 1H), 6.93 (m, 1H), 6.83 (dd, J=4.8 Hz, J=8.8 Hz, 1H), 4.40 (dd, J=4.8 Hz, J=7.2 Hz, 1H), 3.50 (m, 1H), 3.32 (m, 1H), 3.24 (s, 3H), 3.10 (s, 3H), 2.86 (s, 3H), 2.43 (s, 3H), 2.41 (s, 3H).

Example 14

5-[5-Fluoro-2-oxo-1,2-dihydro-indol-(3Z)-ylidenemethyl]-2,4-dimethyl-1H-pyrrole-3-carboxylic acid (2-methoxy-3-morpholin-4-yl-3-oxo-propyl)-amide

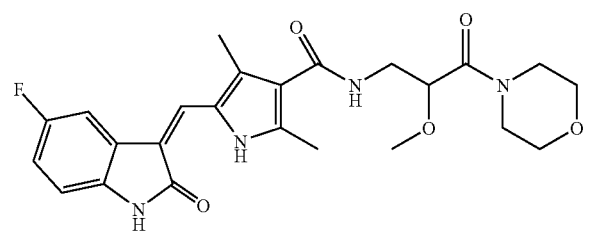

Preparative HPLC gave 98 mg of the title compound (73%) from 115 mg starting material (acid). LC-MS: single peak at 254 nm, MH+ calcd. for $C_{24}H_{27}FN_4O_5$: 471, obtained: 471. $^1$H-NMR (DMSO-d$_6$, 400 MHz), δ 13.67 (s, 1H), 10.89 (s, 1H), 7.75 (dd, J=2.4 Hz, J=9.6 Hz, 1H), 7.71 (s, 1H), 7.70 (m, 1H), 6.92 (m, 1H), 6.83 (dd, J=4.8 Hz, J=8.8 Hz, 1H), 4.34 (dd, J=4.8 Hz, J=7.2 Hz, 1H), 3.85-3.30 (m, 10H), 3.26 (s, 3H), 2.44 (s, 3H), 2.42 (s, 3H).

Example 15

5-[5-Fluoro-2-oxo-1,2-dihydro-indol-(3Z)-ylidenemethyl]-2,4-dimethyl-1H-pyrrole-3-carboxylic acid (2-methoxy-3-oxo-3-pyrrolidin-1-yl-propyl)-amide

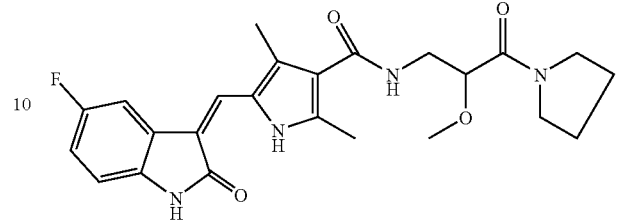

Preparative HPLC gave 86 mg of the title compound (66%) from 115 mg starting material (acid). LC-MS: single peak at 254 nm, MH+ calcd. for $C_{24}H_{27}FN_4O_4$: 455, obtained: 455. $^1$H-NMR (DMSO-d$_6$, 400 MHz), δ 13.67 (s, 1H), 10.89 (s, 1H), 7.76 (dd, J=2.4 Hz, J=9.6 Hz, 1H), 7.70 (m, 1H), 7.71 (s, 1H), 6.93 (m, 1H), 6.83 (dd, J=4.4 Hz, J=8.4 Hz, 1H), 4.20 (dd, J=5.2 Hz, J=7.2 Hz, 1H), 3.60-3.47 (m, 3H), 3.43-3.28 (m, 3H), 3.26 (s, 3H), 2.43 (s, 3H), 2.40 (s, 3H), 1.88 (m, 2H), 1.78 (m, 2H).

Examples 16-315

Still further amide examples are shown in the following table:

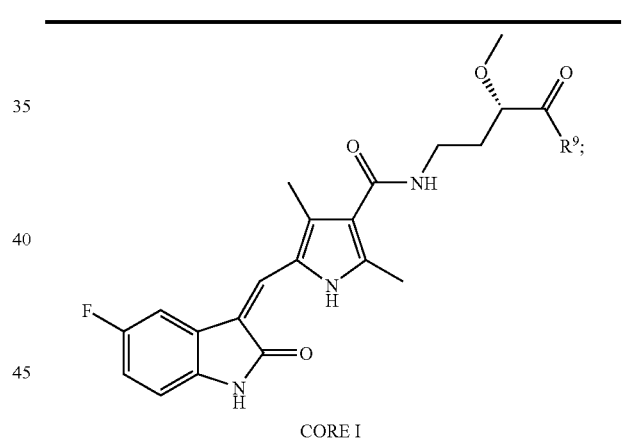

CORE I

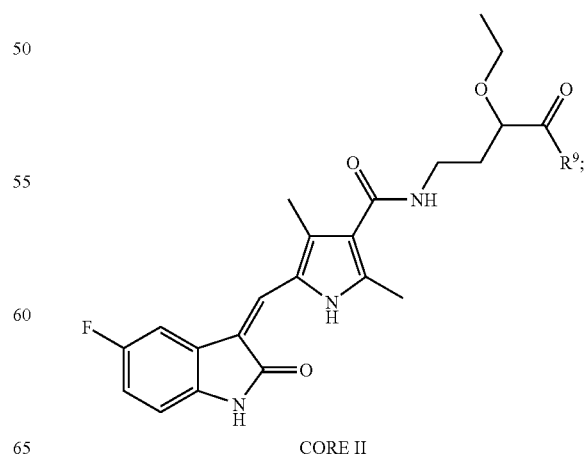

CORE II

-continued

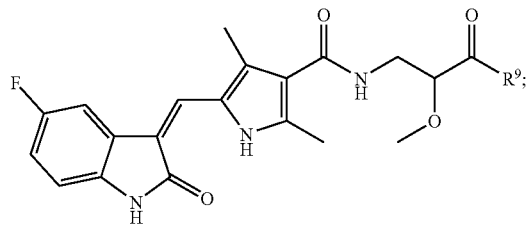

CORE III

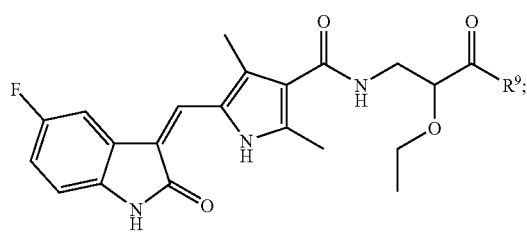

CORE IV

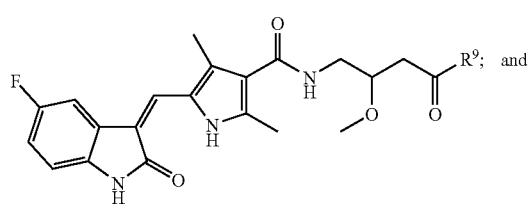

CORE V and

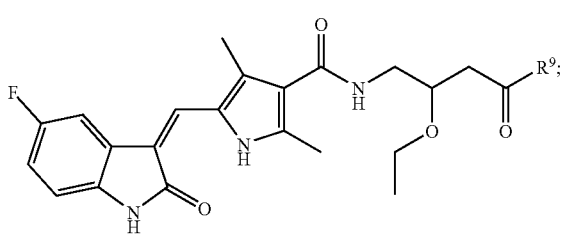

CORE VI

| Ex# | Core | R |
|---|---|---|
| 16 | I | a |
| 17 | I | b |
| 18 | I | c |
| 19 | I | d |
| 20 | I | e |
| 21 | I | f |
| 22 | I | g |
| 23 | I | h |
| 24 | I | i |
| 25 | I | j |
| 26 | I | k |
| 27 | I | l |
| 28 | I | m |
| 29 | I | n |
| 30 | I | o |
| 31 | I | p |
| 32 | I | q |
| 33 | I | r |
| 34 | I | s |
| 35 | I | t |
| 36 | I | u |
| 37 | I | v |
| 38 | I | w |
| 39 | I | x |
| 40 | I | y |

-continued

| | | |
|---|---|---|
| 41 | I | z |
| 42 | I | aa |
| 43 | I | ab |
| 44 | I | ac |
| 45 | I | ad |
| 46 | I | ae |
| 47 | I | af |
| 48 | I | ag |
| 49 | I | ah |
| 50 | I | ai |
| 51 | I | aj |
| 52 | I | ak |
| 53 | I | al |
| 54 | I | am |
| 55 | I | an |
| 56 | I | ao |
| 57 | I | ap |
| 58 | I | aq |
| 59 | I | ar |
| 60 | I | as |
| 61 | I | at |
| 62 | I | au |
| 63 | I | av |
| 64 | I | aw |
| 65 | I | ax |
| 66 | II | a |
| 67 | II | b |
| 68 | II | c |
| 69 | II | d |
| 70 | II | e |
| 71 | II | f |
| 72 | II | g |
| 73 | II | h |
| 74 | II | i |
| 75 | II | j |
| 76 | II | k |
| 77 | II | l |
| 78 | II | m |
| 79 | II | n |
| 80 | II | o |
| 81 | II | p |
| 82 | II | q |
| 83 | II | r |
| 84 | II | s |
| 85 | II | t |
| 86 | II | u |
| 87 | II | v |
| 88 | II | w |
| 89 | II | x |
| 90 | II | y |
| 91 | II | z |
| 92 | II | aa |
| 93 | II | ab |
| 94 | II | ac |
| 95 | II | ad |
| 96 | II | ae |
| 97 | II | af |
| 98 | II | ag |
| 99 | II | ah |
| 100 | II | ai |
| 101 | II | aj |
| 102 | II | ak |
| 103 | II | at |
| 104 | II | am |
| 105 | II | an |
| 106 | II | ao |
| 107 | II | ap |
| 108 | II | aq |
| 109 | II | ar |
| 110 | II | as |
| 111 | II | at |
| 112 | II | au |
| 113 | II | av |
| 114 | II | aw |
| 115 | II | ax |
| 116 | III | a |
| 117 | III | b |
| 118 | III | c |
| 119 | III | d |

-continued

| | | |
|---|---|---|
| 120 | III | e |
| 121 | III | f |
| 122 | III | g |
| 123 | III | h |
| 124 | III | i |
| 125 | III | j |
| 126 | III | k |
| 127 | III | l |
| 128 | III | m |
| 129 | III | n |
| 130 | III | o |
| 131 | III | p |
| 132 | III | q |
| 133 | III | r |
| 134 | III | s |
| 135 | III | t |
| 136 | III | u |
| 137 | III | v |
| 138 | III | w |
| 139 | III | x |
| 140 | III | y |
| 141 | III | z |
| 142 | III | aa |
| 143 | III | ab |
| 144 | III | ac |
| 145 | III | ad |
| 146 | III | ae |
| 147 | III | af |
| 148 | III | ag |
| 149 | III | ah |
| 150 | III | ai |
| 151 | III | aj |
| 152 | III | ak |
| 153 | III | al |
| 154 | III | am |
| 155 | III | an |
| 156 | III | ao |
| 157 | III | ap |
| 158 | III | aq |
| 159 | III | ar |
| 160 | III | as |
| 161 | III | at |
| 162 | III | au |
| 163 | III | av |
| 164 | III | aw |
| 165 | III | ax |
| 166 | IV | a |
| 167 | IV | b |
| 168 | IV | c |
| 169 | IV | d |
| 170 | IV | e |
| 171 | IV | f |
| 172 | IV | g |
| 173 | IV | h |
| 174 | IV | i |
| 175 | IV | j |
| 176 | IV | k |
| 177 | IV | l |
| 178 | IV | m |
| 179 | IV | n |
| 180 | IV | o |
| 181 | IV | p |
| 182 | IV | q |
| 183 | IV | r |
| 184 | IV | s |
| 185 | IV | t |
| 186 | IV | u |
| 187 | IV | v |
| 188 | IV | w |
| 189 | IV | x |
| 190 | IV | y |
| 191 | IV | z |
| 192 | IV | aa |
| 193 | IV | ab |
| 194 | IV | ac |
| 195 | IV | ad |
| 196 | IV | ae |
| 197 | IV | af |
| 198 | IV | ag |

-continued

| | | |
|---|---|---|
| 199 | IV | ah |
| 200 | IV | ai |
| 201 | IV | aj |
| 202 | IV | ak |
| 203 | IV | al |
| 204 | IV | am |
| 205 | IV | an |
| 206 | IV | ao |
| 207 | IV | ap |
| 208 | IV | aq |
| 209 | IV | ar |
| 210 | IV | as |
| 211 | IV | at |
| 212 | IV | au |
| 213 | IV | av |
| 214 | IV | aw |
| 215 | IV | ax |
| 216 | V | a |
| 217 | V | b |
| 218 | V | c |
| 219 | V | d |
| 220 | V | e |
| 221 | V | f |
| 222 | V | g |
| 223 | V | h |
| 224 | V | i |
| 225 | V | j |
| 226 | V | k |
| 227 | V | l |
| 228 | V | m |
| 229 | V | n |
| 230 | V | o |
| 231 | V | p |
| 232 | V | q |
| 233 | V | r |
| 234 | V | s |
| 235 | V | t |
| 236 | V | u |
| 237 | V | v |
| 238 | V | w |
| 239 | V | x |
| 240 | V | y |
| 241 | V | z |
| 242 | V | aa |
| 243 | V | ab |
| 244 | V | ac |
| 245 | V | ad |
| 246 | V | ae |
| 247 | V | af |
| 248 | V | ag |
| 249 | V | ah |
| 250 | V | ai |
| 251 | V | aj |
| 252 | V | ak |
| 253 | V | al |
| 254 | V | am |
| 255 | V | an |
| 256 | V | ao |
| 257 | V | ap |
| 258 | V | aq |
| 259 | V | ar |
| 260 | V | as |
| 261 | V | at |
| 262 | V | au |
| 263 | V | av |
| 264 | V | aw |
| 265 | V | ax |
| 266 | VI | a |
| 267 | VI | b |
| 268 | VI | c |
| 269 | VI | d |
| 270 | VI | e |
| 271 | VI | f |
| 272 | VI | g |
| 273 | VI | h |
| 274 | VI | i |
| 275 | VI | j |
| 276 | VI | k |
| 277 | VI | l |

-continued
| | | |
|---|---|---|
| 278 | VI | m |
| 279 | VI | n |
| 280 | VI | o |
| 281 | VI | p |
| 282 | VI | q |
| 283 | VI | r |
| 284 | VI | s |
| 285 | VI | t |
| 286 | VI | u |
| 287 | VI | v |
| 288 | VI | w |
| 289 | VI | x |
| 290 | VI | y |
| 291 | VI | z |
| 292 | VI | aa |
| 293 | VI | ab |
| 294 | VI | ac |
| 295 | VI | ad |
| 296 | VI | ae |
| 297 | VI | af |
| 298 | VI | ag |
| 299 | VI | ah |
| 300 | VI | ai |
| 301 | VI | aj |
| 302 | VI | ak |
| 303 | VI | al |
| 304 | VI | am |
| 305 | VI | an |
| 306 | VI | ao |
| 307 | VI | ap |
| 308 | VI | aq |
| 309 | VI | ar |
| 310 | VI | as |
| 311 | VI | at |
| 312 | VI | au |
| 313 | VI | av |
| 314 | VI | aw |
| 315 | VI | ax |
In the above table, $R^9$ is selected from the following radicals:
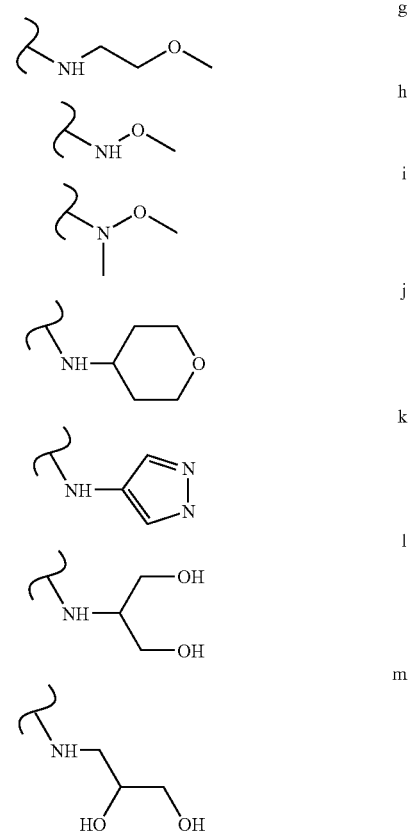
a
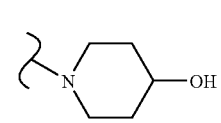
b
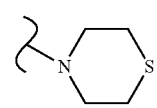
c
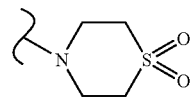
d
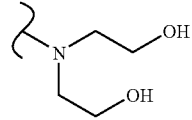
e
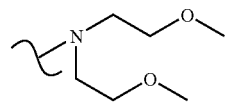
f
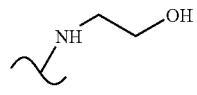

-continued
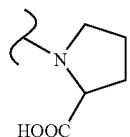 u
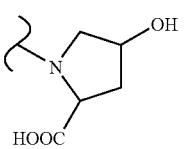 v
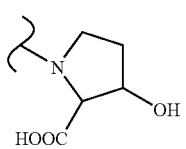 w
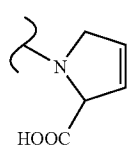 x
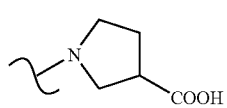 y
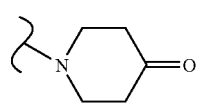 z
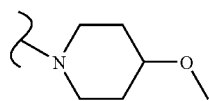 aa
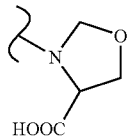 ab
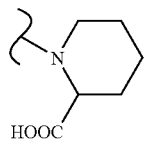 ac
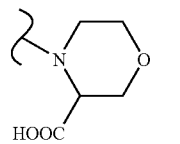 ad
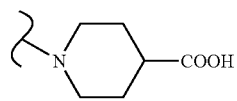 ae
-continued
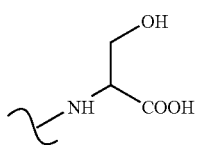 af
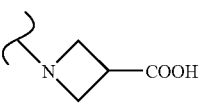 ag
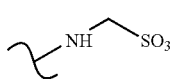 ah
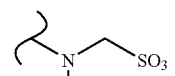 ai
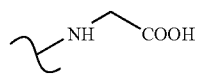 aj
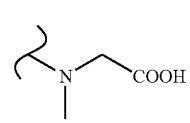 ak
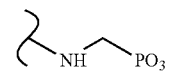 al
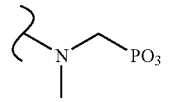 am
 an
 ao
 ap
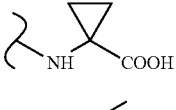 aq
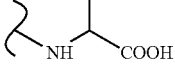 ar
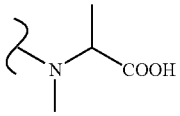 as
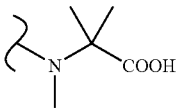

-continued

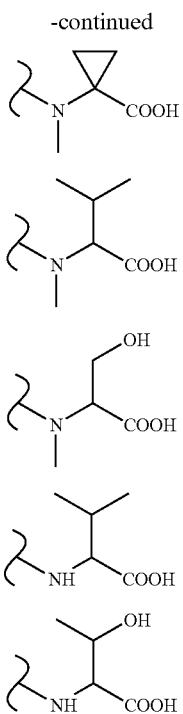

at au av aw ax

These amide examples 16-315 can be made by those skilled in the art following the above procedure and/or known procedures.

Examples 316-320

Figure 3:
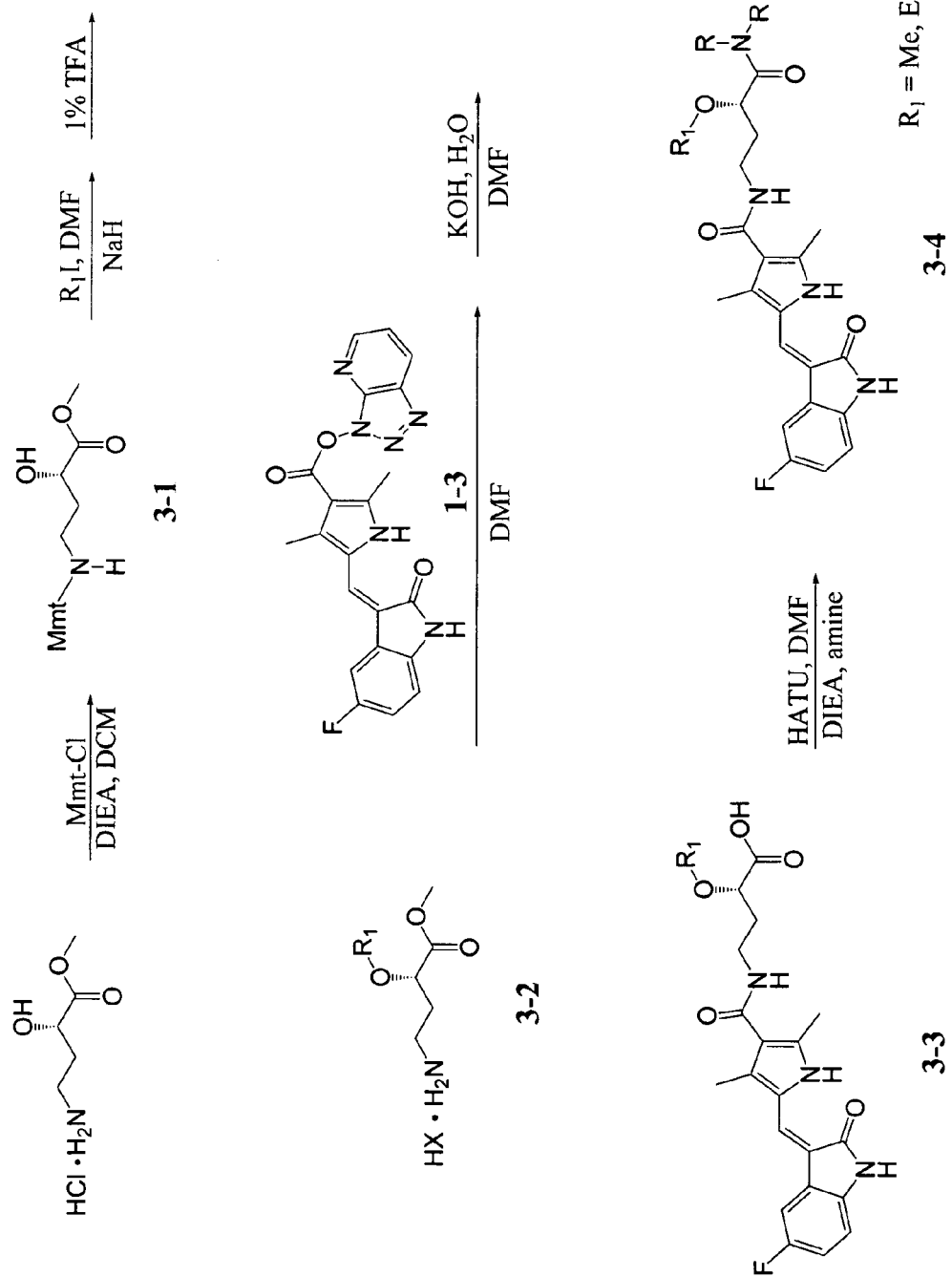
FIG. 3 illustrates a scheme that is used for the synthesis of the (2S)-2-alkoxy-4-acylamino-amide derivatives starting from methyl (2S)-2-hydroxy-4-aminobutanoate hydrochloride and the activated acylating agent 1-3.

The synthesis of acids (3-3) and amides (3-4) is shown in FIG. 3. Variations from this general synthetic procedure can be understood and carried out by those skilled in the art. Thus, the compounds of the present invention can be synthesized by those skilled in the art.

Example 316

(S)-4-({5-[5-Fluoro-2-oxo-1,2-dihydro-indol-(3Z)-ylidenemethyl]-2,4-dimethyl-1H-pyrrole-3-carbonyl}-amino)-2-methoxy-butyric acid

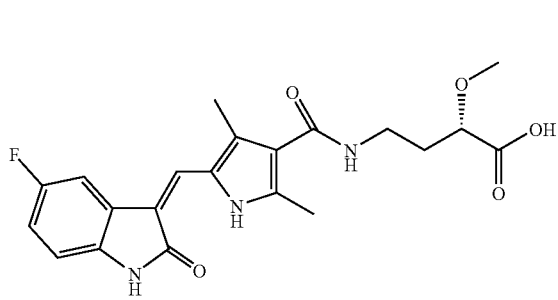

To a suspension of methyl 4-amino-2-hydroxybutyrate (1.0 equiv, which was prepared by refluxing the free amino acid in dry methanol with 1.2 equiv HCl) and DIEA (5 equiv) in DCM, Mmt-Cl (1.1 equiv) was added portion-wise at 25° C. After stirring overnight, the DCM was removed under reduced pressure. The residue was suspended in ethyl acetate, washed with brine (3×), dried over anhydrous $Na_2SO_4$. The ethyl acetate was then removed, and the residue was dried overnight under high vacuum, and subjected to flash chromatography to give compound 3-1. To a solution of compound 3-1 in dry DMF, NaH (1.5 equiv) was added under argon. After stirring at 25° C. for 1 h, MeI (5 equiv) was added to the solution, and the resulting suspension was gently stirred at 25° C. overnight. The DMF was removed under vacuum; the residue was suspended in ethyl acetate, washed with brine (3×), and dried over anhydrous $Na_2SO_4$. After the ethyl acetate was removed via evaporation the resulting residue was treated with 1% TFA in DCE/DCM for 30 min. The organic solvents were then removed under reduced pressure, and the resulting residue was triturated with hexane (3×) to obtain the free amino acid 3-2. This amino acid was used directly in the next step without any purification and characterization. Thus, to a solution of 3-2 (2 equiv) and DIEA (5 equiv) in DMF, compound 1-3 (1 equiv) was added at 25° C. After stirring for 30 min (LC-MS show the complete consumption of 1-3), KOH (5 equiv) in water was added, and the solution was stirred for another 2 h (LC-MS demonstrated a complete hydrolysis). The solvents were removed under reduced pressure, and HCl (1N, excess) was added to give a precipitate. This precipitate was collected and washed (by water) by filtration, dried under high vacuum to give the title compound (97% based on compound 1-3). LC-MS: single peak at 254 nm, $MH^+$ calcd. for $C_{21}H_{22}FN_3O_5$: 416, obtained: 416. $^1$H-NMR (DMSO-$d_6$, 400 MHz), δ 13.68 (s, 1H), 12.80 (b, 1H), 10.90 (s, 1H), 7.76 (dd, J=2.4 Hz, J=9.6 Hz, 1H), 7.71 (s, 1H), 7.65 (t, J=5.6 Hz, 1H), 6.93 (m, 1H), 6.83 (dd, J=4.8 Hz, J=8.4 Hz, 1H), 3.77 (dd, J=4.0 Hz, J=8.8 Hz, 1H), 3.40-3.30 (m, 2H), 3.30 (s, 3H), 2.43 (s, 3H), 2.41 (s, 3H), 1.92 (m, 1H), 1.78 (m, 1H).

Example 317

(S)-2-Ethoxy-4-({5-[5-fluoro-2-oxo-1,2-dihydro-indol-(3Z)-ylidenemethyl]-2,4-dimethyl-1H-pyrrole-3-carbonyl}-amino)-butyric acid

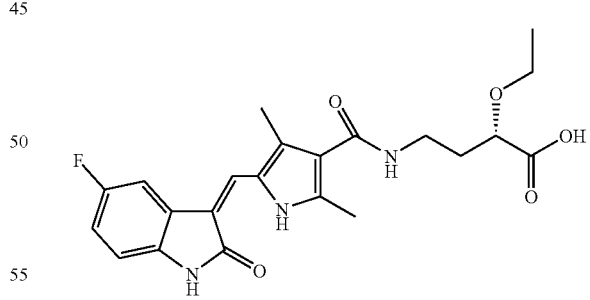

A similar route as that for the synthesis of Example 316 was used to prepare the title compound. Iodoethane was used instead of iodomethane to obtain the 2-ethoxy compound (84% based on compound 1-3). LC-MS: single peak at 254 nm, $MH^+$ calcd. for $C_{22}H_{24}FN_3O_5$: 430, obtained: 430. $^1$H-NMR (DMSO-$d_6$, 400 MHz), δ 13.68 (s, 1H), 12.70 (b, 1H), 10.89 (s, 1H), 7.76 (dd, J=2.4 Hz, J=9.6 Hz, 1H), 7.71 (s, 1H), 7.66 (t, J=5.6 Hz, 1H), 6.93 (m, 1H), 6.83 (dd, J=4.8 Hz, J=8.4 Hz, 1H), 3.85 (dd, J=4.0 Hz, J=8.4 Hz, 1H), 3.58 (m, 1H), 3.40-3.25 (m, 3H), 2.43 (s, 3H), 2.41 (s, 3H), 1.92 (m, 1H), 1.77 (m, 1H), 1.13 (t, J=7.2 Hz, 3H).

Example 318-320

The general procedure for the synthesis of amides (compounds 3-4): A corresponding amine (2 equiv) was added to a solution of the acid (compound 3-3), HATU (1.05 mmol), and DIEA (5 equiv) in DMF (5 mL). After the solution was stirred at 25° C. for 2 h, aqueous HCl (2 mL, 1N) was added. This solution was subjected to preparative HPLC to obtain the pure amide product, which was subsequently characterized by LC-MS and NMR spectroscopy.

Example 318

5-[5-Fluoro-2-oxo-1,2-dihydro-indol-(3Z)-ylidenemethyl]-2,4-dimethyl-1H-pyrrole-3-carboxylic acid ((S)-3-dimethylcarbamoyl-3-methoxy-propyl)-amide

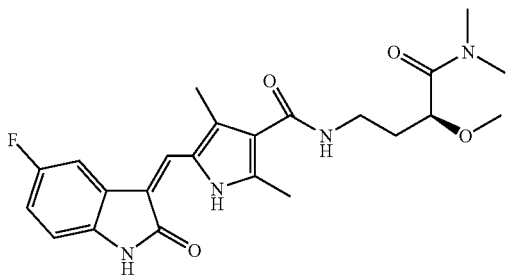

Preparative HPLC gave 37 mg of the title compound (58%) from 60 mg starting material (acid). LC-MS: single peak at 254 nm, MH+ calcd. for $C_{23}H_{27}FN_4O_4$: 443, obtained: 443. $^1$H-NMR (DMSO-$d_6$, 400 MHz), δ 13.68 (s, 1H), 10.89 (s, 1H), 7.76 (dd, J=2.4 Hz, J=9.6 Hz, 1H), 7.72 (s, 1H), 7.65 (t, J=5.6 Hz, 1H), 6.93 (m, 1H), 6.83 (dd, J=4.8 Hz, J=8.4 Hz, 1H), 4.20 (dd, J=4.0 Hz, J=8.0 Hz, 1H), 3.30 (m, 2H), 3.27 (s, 3H), 3.04 (s, 3H), 2.88 (s, 3H), 2.43 (s, 3H), 2.41 (s, 3H), 1.80 (m, 2H).

Example 319

5-[5-Fluoro-2-oxo-1,2-dihydro-indol-(3Z)-ylidenemethyl]-2,4-dimethyl-1H-pyrrole-3-carboxylic acid ((S)-3-methoxy-4-morpholin-4-yl-4-oxo-butyl)-amide

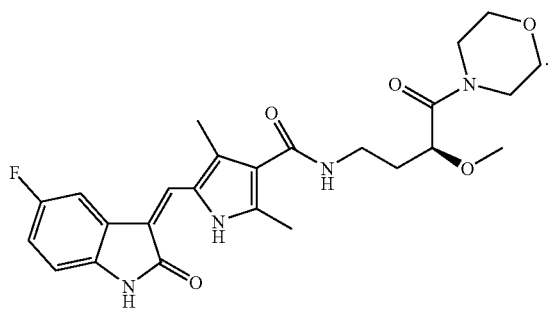

Preparative HPLC gave 32 mg of the title compound (46%) from 60 mg starting material (acid). LC-MS: single peak at 254 nm, MH+ calcd. for $C_{25}H_{29}FN_4O_5$: 485, obtained: 485. $^1$H-NMR (DMSO-$d_6$, 400 MHz), δ 13.68 (s, 1H), 10.89 (s, 1H), 7.76 (dd, J=2.4 Hz, J=9.6 Hz, 1H), 7.72 (s, 1H), 7.65 (t, J=5.6 Hz, 1H), 6.93 (m, 1H), 6.83 (dd, J=4.8 Hz, J=8.4 Hz, 1H), 4.19 (dd, J=4.8 Hz, J=8.0 Hz, 1H), 3.57 (m, 6H), 3.47 (m, 2H), 3.28 (m, 2H), 3.23 (s, 3H), 2.44 (s, 3H), 2.41 (s, 3H), 1.79 (m, 2H).

Example 320

5-[5-Fluoro-2-oxo-1,2-dihydro-indol-(3Z)-ylidenemethyl]-2,4-dimethyl-1H-pyrrole-3-carboxylic acid ((S)-3-dimethylcarbamoyl-3-ethoxy-propyl)-amide

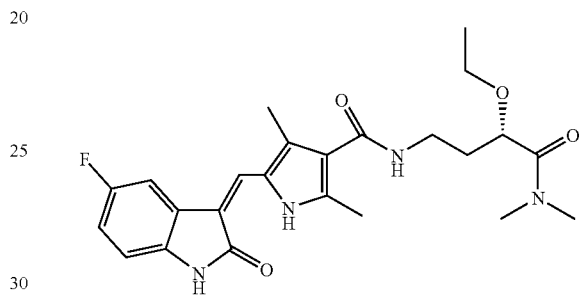

Preparative HPLC gave 67 mg of the title compound (57%) from 120 mg starting material (acid). LC-MS: single peak at 254 nm, MH+ calcd. for $C_{24}H_{29}FN_4O_4$: 457, obtained: 457. $^1$H-NMR (DMSO-$d_6$, 400 MHz), δ 13.67 (s, 1H), 10.88 (s, 1H), 7.76 (dd, J=2.4 Hz, J=9.6 Hz, 1H), 7.71 (s, 1H), 7.56 (m, 1H), 6.91 (m, 1H), 6.83 (m, 1H), 4.25 (m, 1H), 3.45-3.25 (m, 4H), 3.03 (s, 3H), 2.83 (s, 3H), 2.43 (s, 3H), 2.41 (s, 3H), 1.80 (m, 2H).

The compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

VEGFR Biochemical Assay

The compounds were assayed for biochemical activity by Upstate Ltd at Dundee, United Kingdom, according to the following procedure. In a final reaction volume of 25 μl, KDR (h) (5-10 mU) is incubated with 8 mM MOPS pH 7.0, 0.2 mM EDTA, 0.33 mg/ml myelin basic protein, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a P30 filtermat and washed three times for 5 minutes in 75 mM phosphoric acid and once in methanol prior to drying and scintillation counting.

Compounds of the present invention were tested in this assay and exhibited IC$_{50}$ between 1-5,000 nM.

PDGFR Phosphorylation Assay

NIH3T3 cells are plated in a 96 well plate in DMEM+10% FBS. Following cell attachment the cells are serum starved overnight before adding the chemical test compounds to a final concentration of 0.1% DMSO. Following a 1 hour incubation at 37° C. cells are removed from the incubator and allowed to cool to RT for 20 min before stimulation with PDGF-BB for 15 min at RT. Cells are placed on ice for 5 min, the media removed and the cells are lysed with 100 µwell lysis buffer for 1 hour at 4° C. Plates are spun at 2000 rpm for 30 min at 4° C. and solubilized phosphorylated PDGFR is quantitated by ELISA.

High binding microplates are incubated overnight at RT with anti-mouse PDGFR-b capture-antibody in PBS, washed with PBS+0.05% Tween20 and blocked for 4 h at RT with PBS+1% BSA and washed again. 100 µL lysate/well is incubated overnight at 4° C. Plates are washed and wells are incubated with 100 µL/well of mouse anti-phosphotyrosine-HRP antibody for 2 h at 37° C. Plates are washed again and colorimetric detection is performed using TMB as substrate.

Most of the compounds in this invention showed $IC_{50}$ of less than 1 µM in this assay.

VEGFR Phosphorylation Assay

NIHT3T cells overexpressing mouse VEGFR-2 (FLK-1) are plated in a 96 well plate in DMEM+10% FBS. Following cell attachment for 4 hours the cells are serum starved overnight before adding the chemical test compounds to a final concentration of 0.1% DMSO. Following a 1 hour incubation at 37° C. cells are stimulated for 15 min at 37° C. with VEGF165. Cells are placed on ice for 5 min, the media removed, washed once with ice cold PBS and the cells are lysed with 50 µL/well lysis buffer for 1 hour at 4° C. Plates are spun for 10 min at 2000 rpm at 4° C. and solubilized phosphorylated VEGFR is quantitated by ELISA.

High binding microplates are incubated overnight at room temperature with VEGFR antibody in 50 µL PBS, washed with PBS+0.05% Tween20 and blocked for 4 h at RT with PBS+1% BSA and washed again. 50 µL lysate/well is incubated overnight at 4° C. Plates are washed and wells are incubated with 50 µL/well of mouse anti-phosphotyrosine-HRP antibody for 2 h at 37° C. Plates are washed again and colorimetric detection is performed using TMB as substrate.

Most of the compounds in this invention showed $IC_{50}$ of less than 1 µM in this assay.

Cellular Assay: HUVEC: VEGF Induced Proliferation

The compounds were assayed for cellular activity in the VEGF induced proliferation of HUVEC cells. HUVEC cells (Cambrex, CC-2517) were maintained in EGM (Cambrex, CC-3124) at 37° C. and 5% $CO_2$. HUVEC cells were plated at a density 5000 cells/well (96 well plate) in EGM. Following cell attachment (1 hour) the EGM-medium was replaced by EBM (Cambrex, CC-3129) +0.1% FBS (ATTC, 30-2020) and the cells were incubated for 20 hours at 37° C. The medium was replaced by EBM +1% FBS, the compounds were serial diluted in DMSO and added to the cells to a final concentration of 0-5,000 nM and 1% DMSO. Following a 1 hour pre-incubation at 37° C. cells were stimulated with 10 ng/ml VEGF (Sigma, V7259) and incubated for 45 hours at 37° C. Cell proliferation was measured by BrdU DNA incorporation for 4 hours and BrdU label was quantitated by ELISA (Roche kit, 16472229) using 1M $H_2SO_4$ to stop the reaction. Absorbance was measured at 450 nm using a reference wavelength at 690 nm.

DETAILED DESCRIPTION OF FIGURES

FIG. 1 shows a scheme that is used for the synthesis of the 3-alkoxy-4-acylaminoamide derivatives starting from methyl 3-hydroxy-4-aminobutanoate hydrochlorides and the activated acylating agent 1-3. The amino ester hydrochloride starting material was prepared by refluxing the free amino acid in anhydrous methanol in the presence of 1.2 eq of HCl. The amino group was protected as its monomethoxytrityl derivative in the presence of the secondary hydroxyl group to give the neutral hydroxy ester 1-1. The hydroxyl group was alkylated using methyl- or ethyl iodide to form the protected amino alkoxy ester. The Mmt group was removed in 1% trifluoroacetic acid leaving the amino hydrochloride or trifluoracetate compound 1-2. This compound was quickly acylated with the preformed acylating agent 1-3 and the methyl ester was hydrolyzed by potassium hydroxide in water/DMF to give 1-4. The free acid was then exposed to HATU, amine and diisopropylethyl amine in DMF to give the alkoxy amide 1-5.

FIG. 2 shows a scheme that is used for the synthesis of the 2-alkoxy-3-acylaminoamide derivatives starting from methyl 2-hydroxy-3-aminopropionate hydrochlorides and the activated acylating agent 1-3. The amino ester hydrochloride starting material was prepared by refluxing the free amino acid in anhydrous methanol in the presence of 1.2 eq of HCl. The amino group was protected as its monomethoxytrityl derivative in the presence of the secondary hydroxyl group to give 2-1. The hydroxyl group was alkylated using methyl- or ethyl iodide to form the protected amino alkoxy ester. The Mmt group was removed in 1% trifluoroacetic acid leaving the amino hydrochloride or trifluoracetate compound 2-2. This compound was quickly acylated with the preformed acylating agent 1-3 and the methyl ester was hydrolyzed by potassium hydroxide in water/DMF to give 2-4. The free acid was then exposed to HATU, amine and diisopropylethyl amine in DMF to give the alkoxy amide 2-5.

FIG. 3 shows a scheme that is used for the synthesis of the (2S)-2-alkoxy-4-acylamino-amide derivatives starting from methyl (2S)-2-hydroxy-4-aminobutanoate hydrochloride and the activated acylating agent 1-3. The amino ester hydrochloride starting material was prepared by refluxing the free amino acid in anhydrous methanol in the presence of 1.2 eq of HCl. The amino group was protected as its monomethoxytrityl derivative in the presence of the secondary hydroxyl group to give the neutral hydroxy ester 3-1. The hydroxyl group was alkylated using methyl- or ethyl iodide to form the protected amino alkoxy ester. The Mmt group was removed in 1% trifluoroacetic acid leaving the amino hydrochloride or trifluoracetate compound 3-2. This compound was quickly acylated with the preformed acylating agent 1-3 and the methyl ester was hydrolyzed by potassium hydroxide in water/DMF to give 3-4. The free acid was then exposed to HATU, amine and diisopropylethyl amine in DMF to give the alkoxy amide 3-5.

What is claimed is:

1. A compound represented by Formula (I):

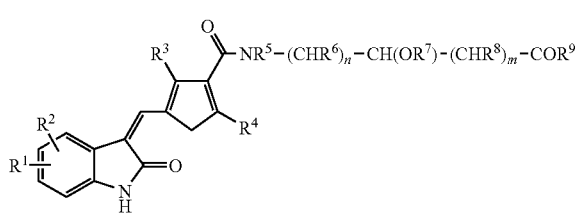

Formula I wherein:
- $R^1$ is selected from the group consisting of hydrogen, halo, (C1-C6) alkyl, (C3-C8) cycloalkyl, (C1-C6) haloalkyl, hydroxy, (C1-C6) alkoxy, amino, (C1-C6) alkylamino, amide, sulfonamide, cyano, substituted or unsubstituted (C6-C10) aryl;
- $R^2$ is selected from the group consisting of hydrogen, halo, (C1-C6) alkyl, (C3-C8) cycloalkyl, (C1-C6) haloalkyl, hydroxy, (C1-C6) alkoxy, (C2-C8) alkoxyalkyl, amino, (C1-C6) alkylamino, (C6-C10) arylamino;
- $R^3$ is selected from the group consisting of hydrogen, (C1-C6) alkyl, (C6-C10) aryl, (C5-C10) heteroaryl, and amide;
- $R^4$, $R^5$, $R^6$ and $R^8$ are independently selected from the group consisting of hydrogen and (C1-C6) alkyl;
- $R^7$ is (C1-C6) alkyl;
- $R^9$ is selected from the group consisting of hydroxy, (C1-C6) O-alkyl, (C3-C8) O-cycloalkyl, and $NR^{10}R^{11}$; where $R^{10}$ and $R^{11}$ are independently selected from the group consisting of hydrogen, (C1-C6) alkyl, (C1-C6) hydroxyalkyl, (C2-C6) dihydroxyalkyl, (C1-C6) alkoxy, (C2-C6) alkyl carboxylic acid, (C1-C6) alkyl phosphonic acid, (C1-C6) alkyl sulfonic acid, (C2-C6) hydroxyalkyl carboxylic acid, (C1-C6) alkyl amide, (C3-C8) cycloalkyl, (C5-C8) heterocycloalkyl, (C6-C8) aryl, (C5-C8) heteroaryl, (C3-C8) cycloalkyl carboxylic acid, or $R^{10}$ and $R^{11}$ together with N forms a (C5-C8) heterocyclic ring either unsubstituted or substituted with one or more hydroxyls, ketones, ethers, and carboxylic acids;
- n is 1, 2, or 3; and
- m is 0, 1, or 2;

or, a pharmaceutically acceptable salt, its tautomer, or a pharmaceutically acceptable salt of its tautomer.

2. The compound, salt, or tautomer according to claim 1 represented by Formula (II):

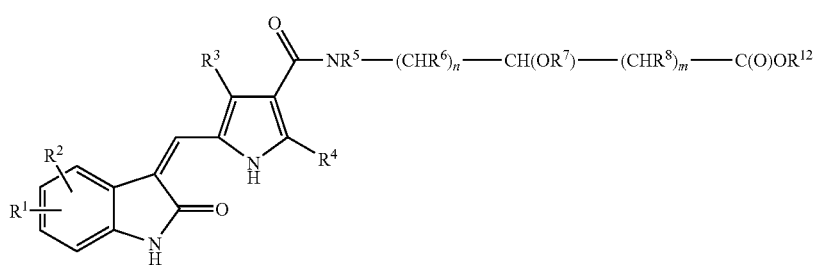

Formula II wherein $R^{12}$ is selected from the group consisting of hydrogen, (C1-C6) alkyl, and (C3-C8) cycloalkyl.

3. The compound, salt, or tautomer according to claim 2, wherein:
- $R^1$ and $R^2$ are independently selected from the group consisting of hydrogen and fluoro;
- $R^3$ and $R^4$ are methyl;
- $R^5$, $R^6$, $R^8$, and $R^{12}$ are hydrogen;
- $R^7$ is (C1-C6) alkyl;
- n is 1 or 2; and
- m is 0 or 1.

4. The compound, salt, or tautomer according to claim 3 selected from the group consisting of:

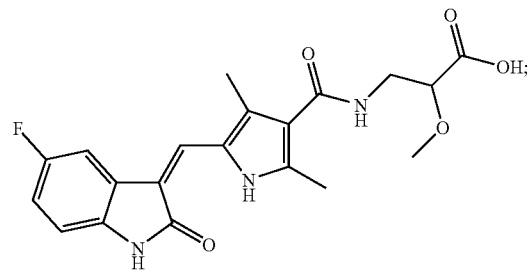

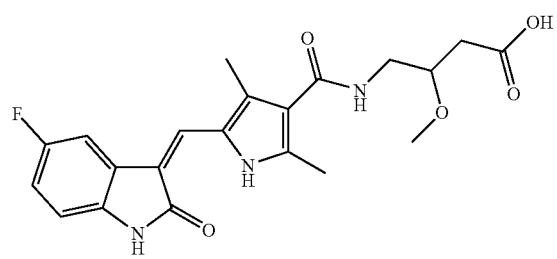

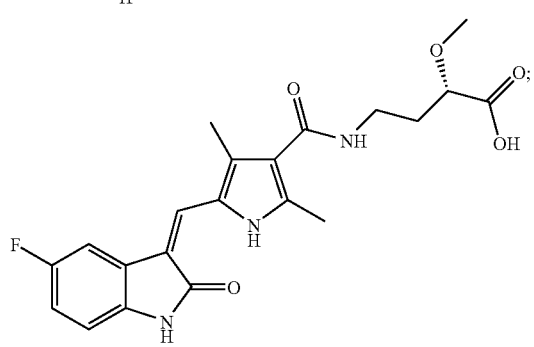

-continued

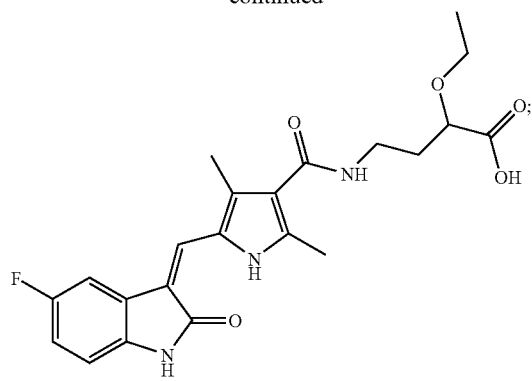

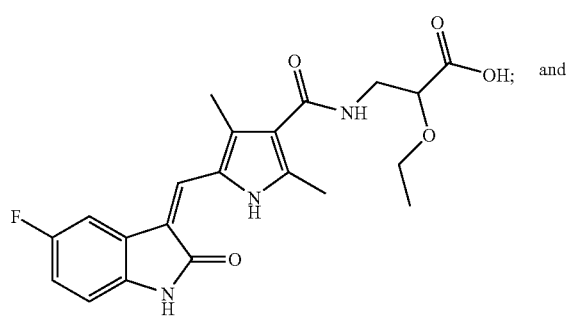; and

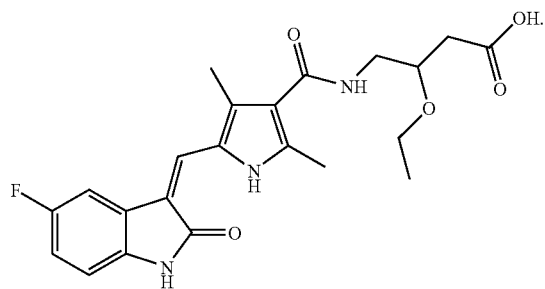

5. The compound salt, or tautomer according to claim 3 represented by the following structure:

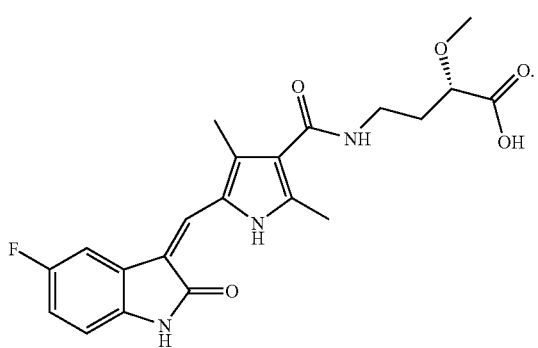

6. The compound, salt, or tautomer according to claim 3 represented by the following structure:

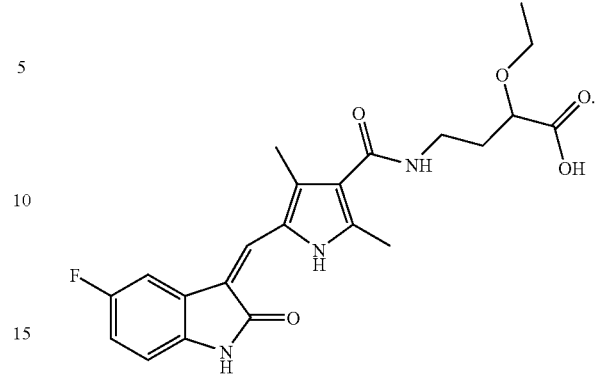

7. The compound, salt, or tautomer according to claim 3 represented by the following structure:

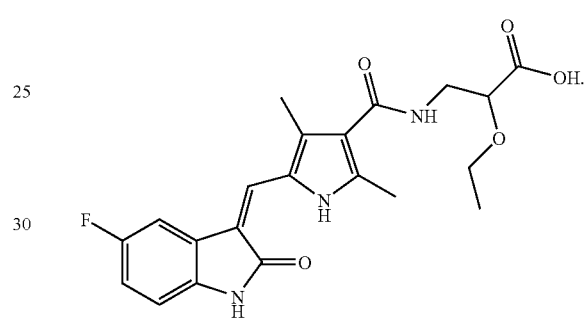

8. The compound, salt, or tautomer according to claim 3 represented by the following structure:

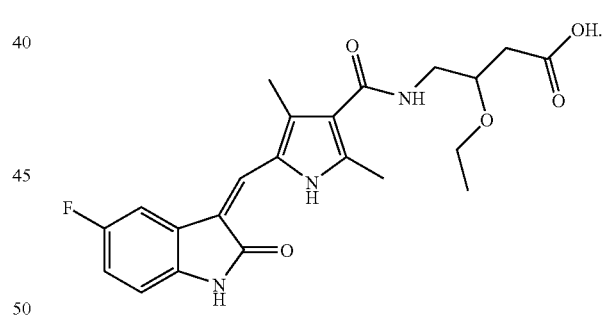

9. The compound, salt, or tautomer according to claim 3 represented by the following structure:

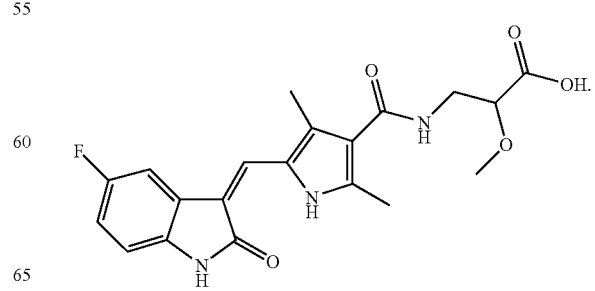

10. The compound, salt, or tautomer according to claim 3 represented by the following structure:

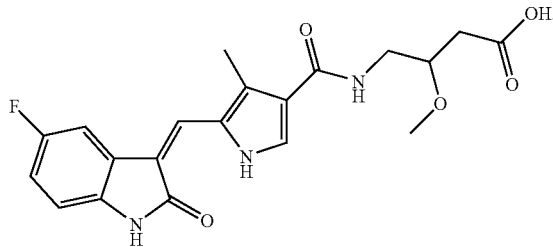

11. A compound, salt, or tautomer according to claim 1 represented by Formula (III):

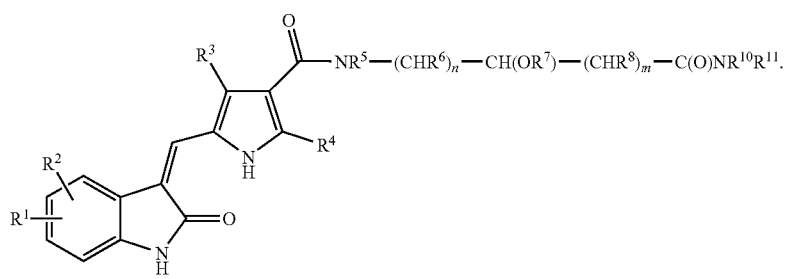

Formula III

12. The compound, salt, or tautomer of claim 9, wherein:

$R^1$ and $R^2$ are independently selected from the group consisting of hydrogen, halo, cyano;

$R^3$ is selected from the group consisting of hydrogen, (C1-C6) alkyl, (C6-C10) aryl, (C5-C10) heteroaryl, and amide;

$R^4$, $R^5$, $R^6$ and $R^8$ are independently selected from the group consisting of hydrogen and (C1-C6) )alkyl;

$R^7$ is (C1-C6) alkyl;

n is 1 or 2;

m is 0 or 1; and $R^{10}$ and $R^{11}$ are selected from the group consisting of hydrogen, (C1-C6) alkyl, (C1-C6) hydroxyalkyl, (C2-C6) dihydroxyalkyl, (C1-C6) alkoxy, (C2-C6) alkyl carboxylic acid, (C1-C6) alkyl phosphonic acid, (C1-C6) alkyl sulfonic acid, (C2-C6) hydroxyalkyl carboxylic acid, (C1-C6) alkyl amide, (C3-C8) cycloalkyl, (C5-C8) heterocycloalkyl, (C6-C8) aryl, (C5-C8) heteroaryl, (C4-C8) cycloalkyl carboxylic acid, or $R^{10}$ and $R^{11}$ together with N forms a (C5-C8) heterocyclic ring either unsubstituted or substituted with one or more hydroxyls, ketones, ethers, and carboxylic acids.

13. The compound, salt, or tautomer according to claim 12 wherein m is 0.

14. The compound, salt, or tautomer according to claim 13 selected from the group represented by the following structures:

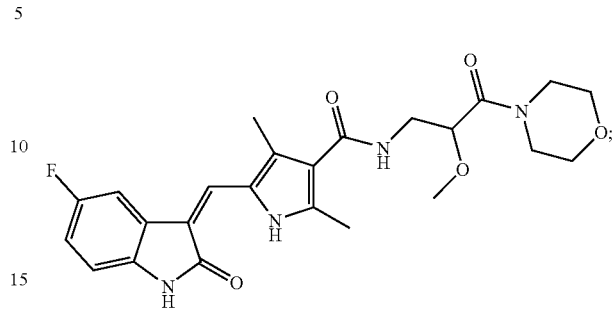

-continued

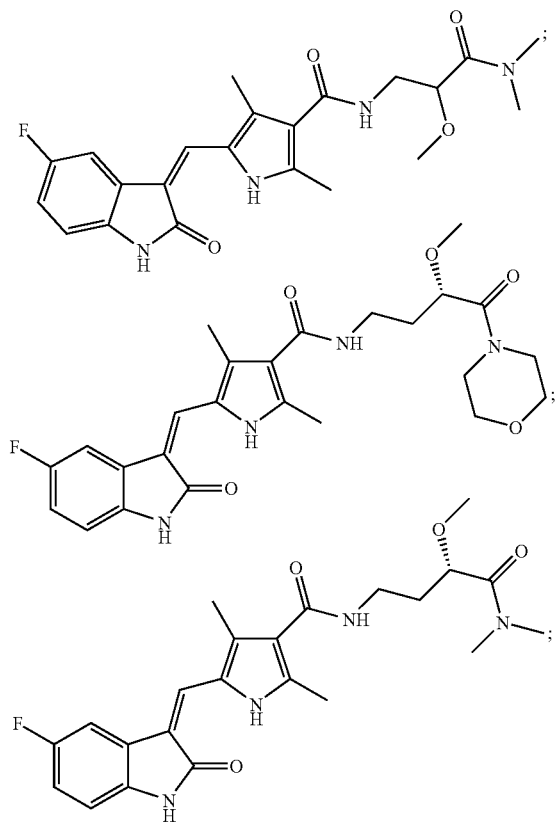

-continued

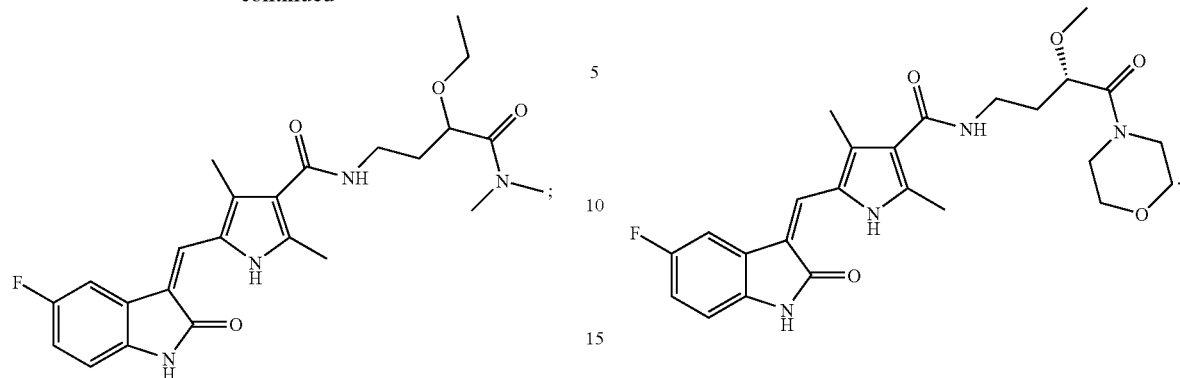

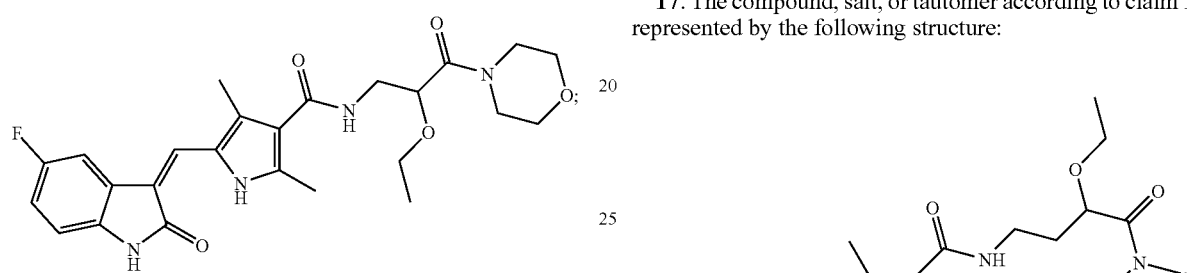

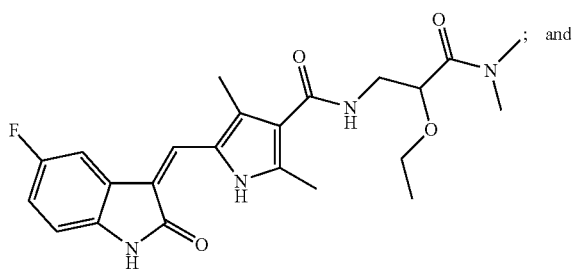

15. The compound, salt, or tautomer according to claim 14 represented by the following structure:

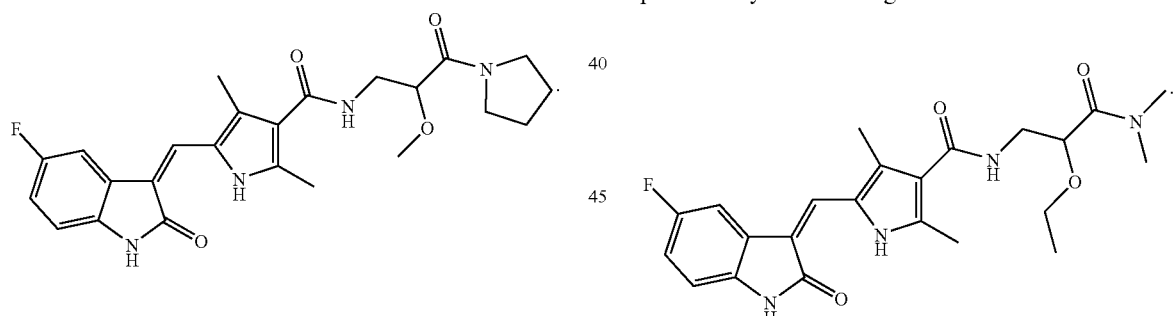

16. The compound, salt, or tautomer according to claim 14 represented by the following structure:

17. The compound, salt, or tautomer according to claim 14 represented by the following structure:

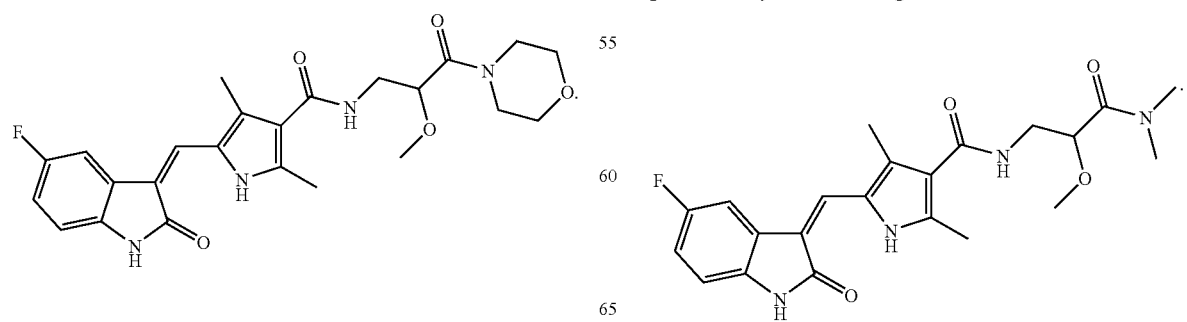

18. The compound, salt, or tautomer according to claim 14 represented by the following structure:

19. The compound, salt, or tautomer according to claim 14 represented by the following structure:

20. The compound, salt, or tautomer according to claim 14 represented by the following structure:

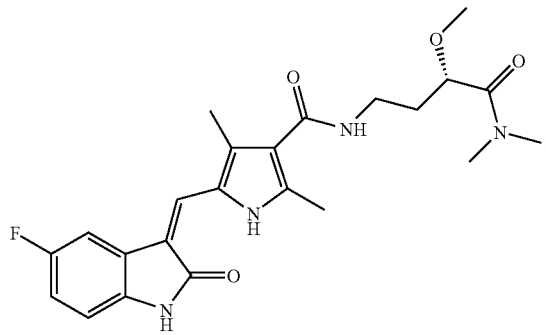

21. The compound, salt, or tautomer according to claim 14 represented by the following structure:

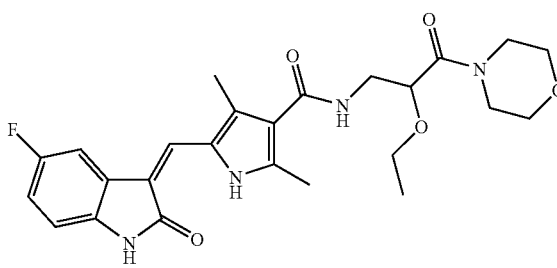

22. The compound, salt, or tautomer according to claim 14 represented by the following structure:

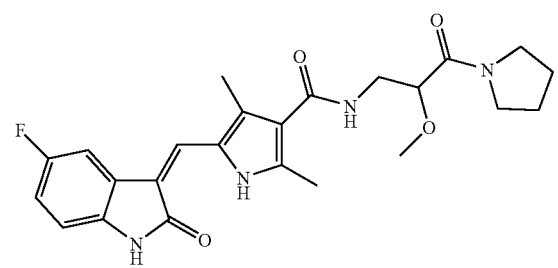

23. The compound, salt, or tautomer according to claim 12 wherein m is 1.

24. The compound, salt, or tautomer according to claim 23 represented by the following structures:

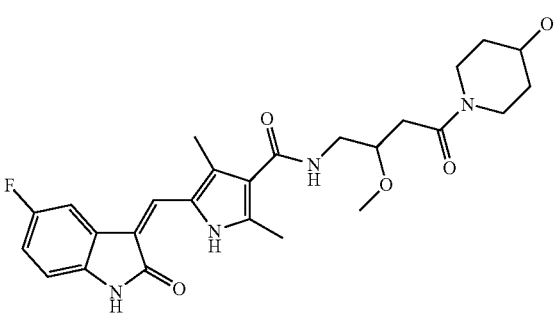

-continued

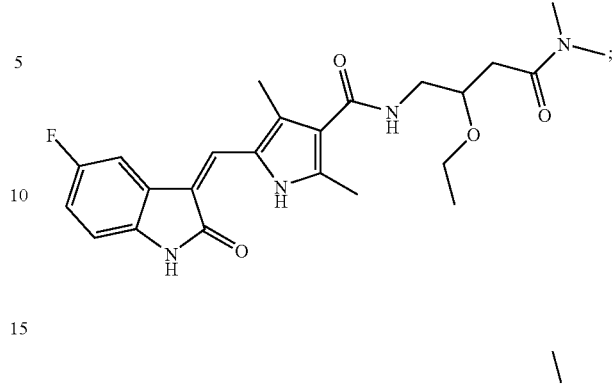

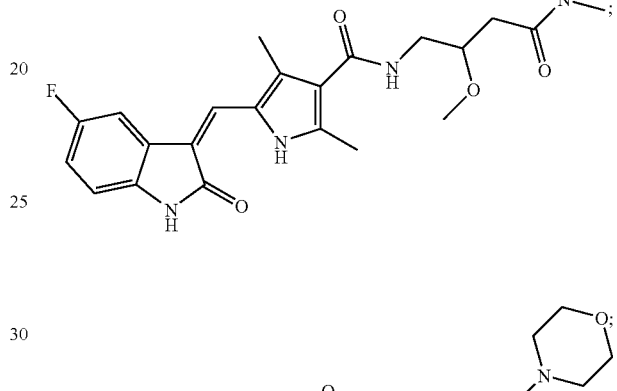

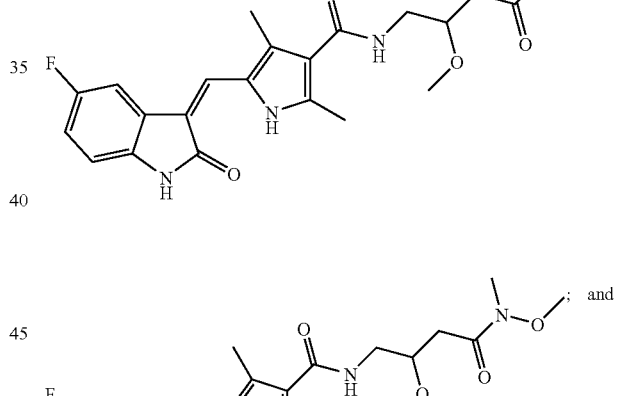

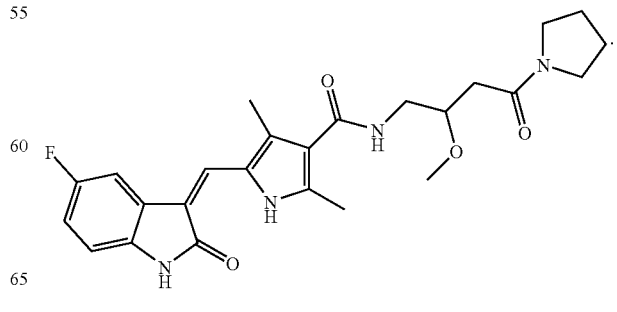

25. The compound, salt, or tautomer according to claim 24 represented by the following structure:

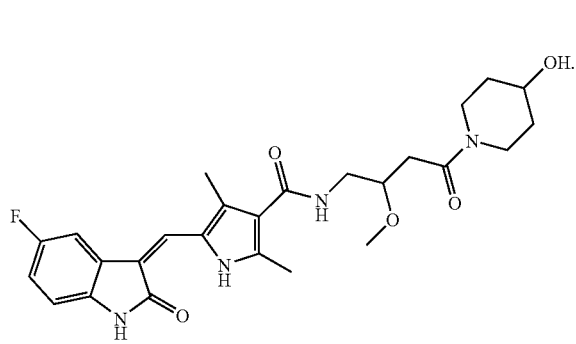

26. The compound, salt, or tautomer according to claim 24 represented by the following structure:

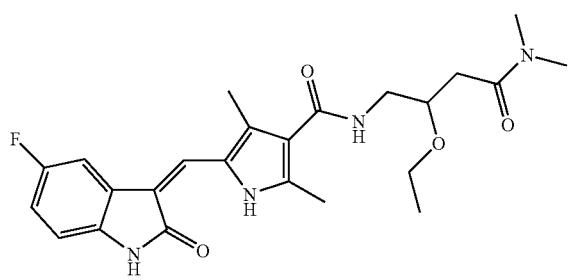

27. The compound, salt, or tautomer according to claim 24 represented by the following structure:

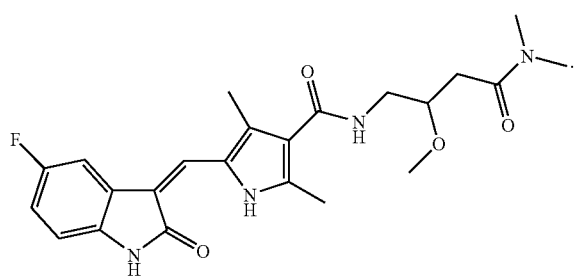

28. The compound, salt, or tautomer according to claim 24 represented by the following structure:

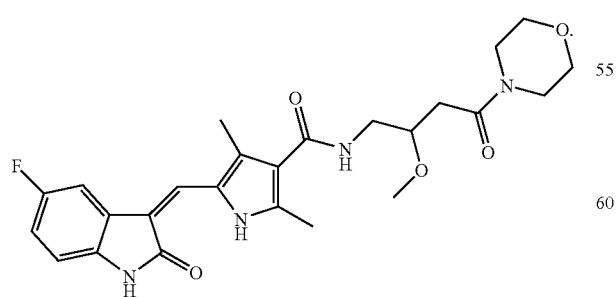

29. The compound, salt, or tautomer according to claim 24 represented by the following structure:

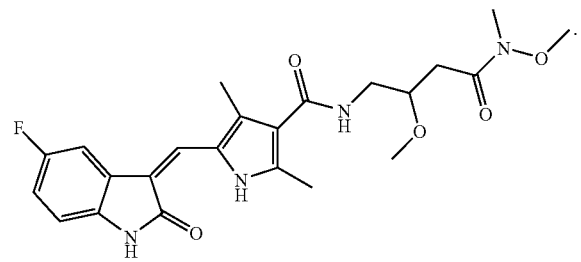

30. The compound, salt, or tautomer according to claim 24 represented by the following structure:

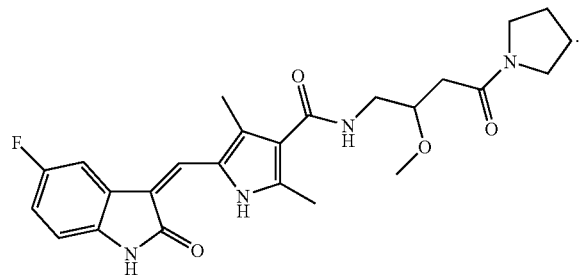

31. The compound, salt, or tautomer according to claim 1 selected from the group represented by the following structures:

CORE I

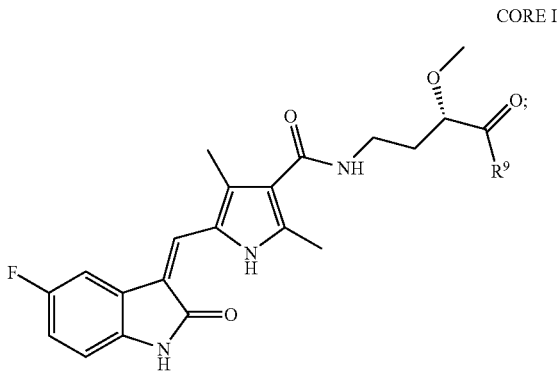

CORE II

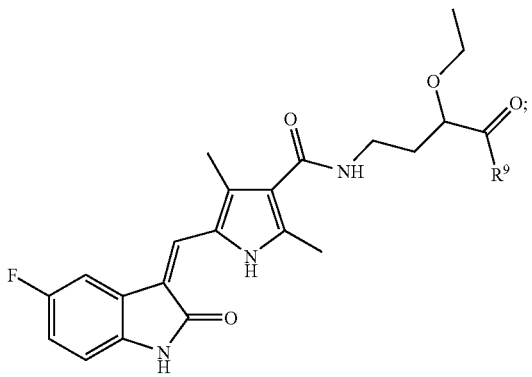

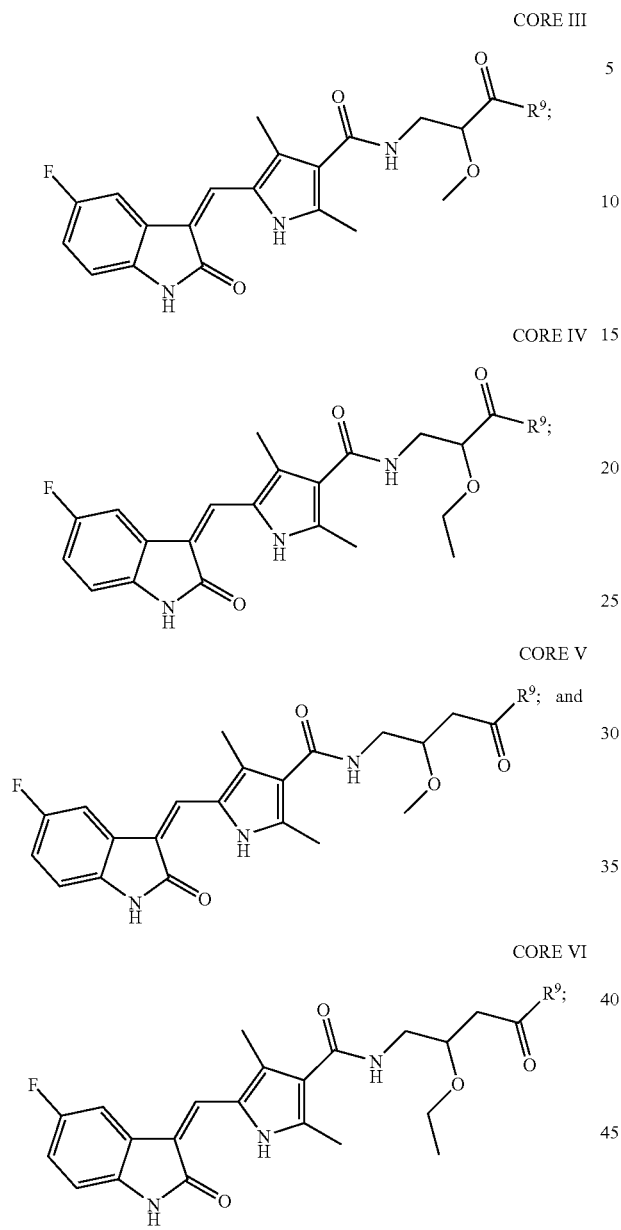
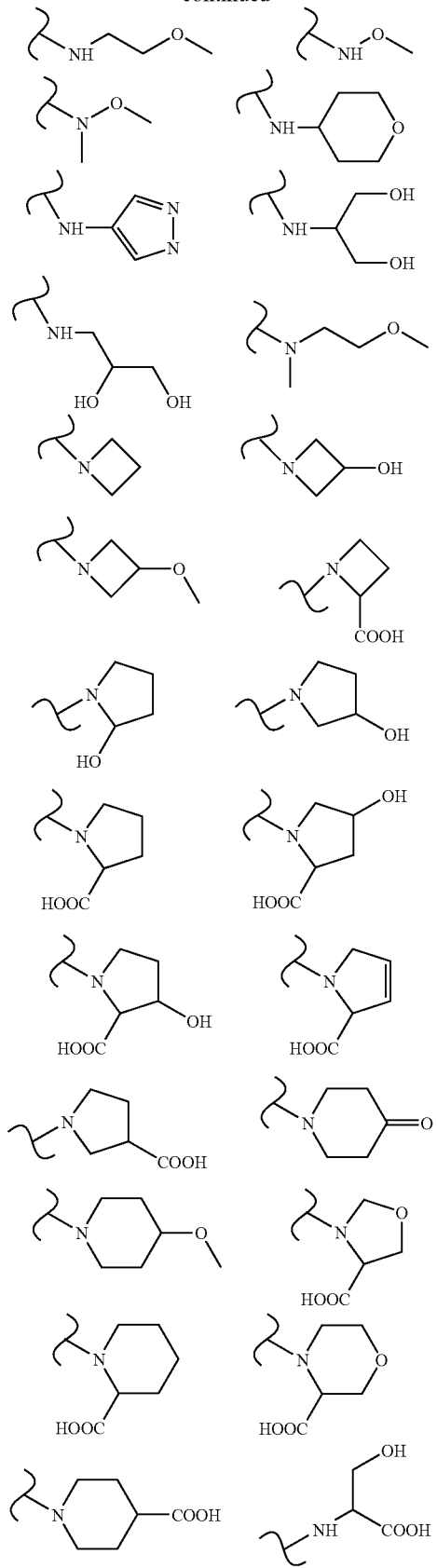
wherein: R⁹ is selected from the group consisting of radical represented by the following structures:

-continued
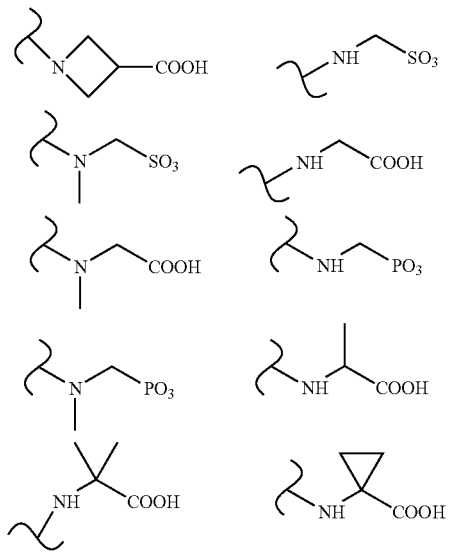
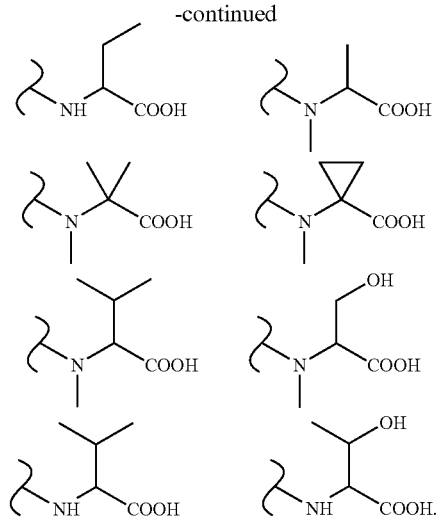
* * * * *

UNITED STATES PATENT AND TRADEMARK OFFICE
CERTIFICATE OF CORRECTION

PATENT NO.       : 7,629,339 B2                                    Page 1 of 1
APPLICATION NO.  : 11/525291
DATED            : December 8, 2009
INVENTOR(S)      : Congxin Liang et al.

It is certified that error appears in the above-identified patent and that said Letters Patent is hereby corrected as shown below:

In column 32, lines 21-22, delete "trifluoracetate" and insert -- trifluoroacetate --, therefor.

In column 32, line 41, delete "trifluoracetate" and insert -- trifluoroacetate --, therefor.

In column 32, lines 60-61, delete "trifluoracetate" and insert -- trifluoroacetate --, therefor.

In column 35, line 48, in Claim 5, delete "compound" and insert -- compound, --, therefor.

In column 37, line 45, in Claim 12, after "(C1-C6)" delete ")".

In column 43, line 25, in Claim 26, after " 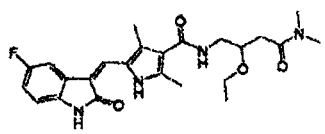 " insert -- . --.

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,629,339 B2  Page 1 of 1
APPLICATION NO. : 11/525291
DATED : December 8, 2009
INVENTOR(S) : Liang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 664 days.

Signed and Sealed this

Twenty-first Day of December, 2010

David J. Kappos
*Director of the United States Patent and Trademark Office*